(12) United States Patent
Johnson et al.

(10) Patent No.: US 11,006,878 B2
(45) Date of Patent: May 18, 2021

(54) MODULATION OF MENTAL STATE OF A USER USING A NON-INVASIVE BRAIN INTERFACE SYSTEM AND METHOD

(71) Applicant: HI LLC, Los Angeles, CA (US)

(72) Inventors: Bryan Johnson, Culver City, CA (US); Husam Katnani, Braintree, MA (US); Antonio H. Lara, Sherman Oaks, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/835,972

(22) Filed: Mar. 31, 2020

(65) Prior Publication Data

US 2020/0315510 A1    Oct. 8, 2020

Related U.S. Application Data

(60) Provisional application No. 62/829,124, filed on Apr. 4, 2019.

(51) Int. Cl.

| | |
|---|---|
| A61B 5/16 | (2006.01) |
| G06F 3/01 | (2006.01) |
| G16B 40/30 | (2019.01) |
| G16B 5/30 | (2019.01) |
| G11B 27/00 | (2006.01) |
| A61B 5/00 | (2006.01) |
| A61B 5/38 | (2021.01) |
| A61B 5/375 | (2021.01) |
| A61B 5/377 | (2021.01) |
| A61B 5/378 | (2021.01) |

(52) U.S. Cl.
CPC .............. *A61B 5/165* (2013.01); *A61B 5/375* (2021.01); *A61B 5/377* (2021.01); *A61B 5/378* (2021.01); *A61B 5/38* (2021.01); *A61B 5/6803* (2013.01); *G06F 3/015* (2013.01); *G11B 27/00* (2013.01); *G16B 5/30* (2019.02); *G16B 40/30* (2019.02); *G05B 2219/39292* (2013.01); *G06F 2203/011* (2013.01)

(58) Field of Classification Search
None
See application file for complete search history.

(56) References Cited

U.S. PATENT DOCUMENTS

| | | | |
|---|---|---|---|
| 5,377,100 A | 12/1994 | Pope et al. | |
| 5,720,619 A | 2/1998 | Fisslinger | |
| 5,853,370 A | 12/1998 | Chance et al. | |
| 6,488,617 B1 | 12/2002 | Katz | |
| 8,209,224 B2 | 6/2012 | Pradeep et al. | |
| 8,473,024 B2 | 6/2013 | Causevic et al. | |
| 8,609,162 B2 | 12/2013 | Giuliano et al. | |
| 8,762,202 B2 | 6/2014 | Pradeep et al. | |
| 9,101,279 B2 | 8/2015 | Ritchey et al. | |
| 9,114,140 B2 | 8/2015 | Giuliano et al. | |
| 9,265,974 B2 | 2/2016 | You et al. | |
| 9,339,227 B2 | 5/2016 | Darcy et al. | |
| 9,417,106 B2 | 8/2016 | Tobita | |
| 9,440,064 B2 | 9/2016 | Wingeier et al. | |
| 9,704,205 B2 | 7/2017 | Akutagawa et al. | |
| 9,712,736 B2 | 7/2017 | Kearns et al. | |
| 9,729,252 B2 | 8/2017 | Tyler et al. | |
| 9,736,603 B2 | 8/2017 | Osborne et al. | |
| 9,943,698 B2 | 4/2018 | Chase et al. | |
| 9,946,344 B2 | 4/2018 | Ayaz et al. | |
| D817,553 S | 5/2018 | Aaskov et al. | |
| D825,112 S | 8/2018 | Saez | |
| 10,091,554 B1 | 10/2018 | Newell et al. | |
| 10,143,414 B2 | 12/2018 | el Kaliouby et al. | |
| 10,188,860 B2 | 1/2019 | Wingeier et al. | |
| 10,234,942 B2 | 3/2019 | Connor | |
| 10,258,760 B1 | 4/2019 | Sherpa et al. | |
| 2003/0176806 A1 | 9/2003 | Pineda et al. | |
| 2004/0049134 A1 | 3/2004 | Tosaya et al. | |
| 2006/0150989 A1 | 7/2006 | Migaly | |
| 2006/0161218 A1 | 7/2006 | Danilov | |

(Continued)

FOREIGN PATENT DOCUMENTS

| | | |
|---|---|---|
| WO | WO02043564 | 6/2002 |
| WO | WO2012135068 | 10/2012 |

(Continued)

OTHER PUBLICATIONS

Stefan K. Ehrlich, et al., "A closed-loop, music-based brain-computer interface for emotion mediation," PLoS ONE 14(3): e0213516. https://doi.org/10.1371/journal.pone.0213516; Mar. 18, 2019.

Patrick Gomez, et al., "Relationships Between Musical Structure and Psychophysiological Measures of Emotion", American Psychological Association, vol. 7, No. 2, 2007, pp. 377-387, 10 pages.

Fernando Lopes da Silva, "EEG and MEG: Relevance to Neuroscience", Center of Neuroscience; http://dx.doi.org/10.1016/j.neuron.2013.10.017; 17 pages.

Elena Boto, et al., "A new generation of magnetoencephalography: Room temperature measurements using optically-pumped magnetometers", NeuroImage 149 (2017) 404-414; 11 pages.

(Continued)

*Primary Examiner* — G Steven Vanni
(74) *Attorney, Agent, or Firm* — Michael J. Bolan; Vista IP Law Group, LLP

(57) ABSTRACT

Brain activity of a user is detected, and a mental state of the user is determined. In one technique, life/work context is automatically presented to the user in a manner that modulates the mental state of the user. In another technique, an entertainment selection is presented to the user, and an entertainment selection list is automatically modified in response to the determined mental state of the user. In still another technique, the mental state that is determined is a negative emotional state, and life/work context is automatically presented to the user in a manner that promotes a cognitive state of the user in response to the determined emotional state of the user. In yet another technique, the wellness of the user is automatically tracked over a time period based on the determined mental state.

26 Claims, 16 Drawing Sheets

(56) References Cited

U.S. PATENT DOCUMENTS

| | | |
|---|---|---|
| 2008/0177197 A1 | 7/2008 | Lee et al. |
| 2009/0083129 A1 | 3/2009 | Pradeep et al. |
| 2012/0172743 A1 | 7/2012 | Aguilar et al. |
| 2013/0289385 A1 | 10/2013 | Lozano et al. |
| 2013/0297599 A1 | 11/2013 | Henshall |
| 2013/0311132 A1 | 11/2013 | Tobita |
| 2014/0023999 A1 | 1/2014 | Greder |
| 2014/0200432 A1 | 7/2014 | Banerji et al. |
| 2014/0228701 A1 | 8/2014 | Chizeck et al. |
| 2014/0303450 A1 | 10/2014 | Caponi |
| 2015/0248651 A1 | 9/2015 | Akutagawa et al. |
| 2015/0290454 A1 | 10/2015 | Tyler et al. |
| 2015/0297109 A1 | 10/2015 | Garten |
| 2015/0338917 A1 | 11/2015 | Steiner et al. |
| 2015/0355462 A1 | 12/2015 | Saito et al. |
| 2016/0077547 A1 | 3/2016 | Aimone |
| 2016/0220163 A1 | 8/2016 | Yamada |
| 2016/0242690 A1 | 8/2016 | Principe et al. |
| 2016/0270656 A1 | 9/2016 | Samec et al. |
| 2017/0042439 A1 | 2/2017 | Yeow |
| 2017/0188876 A1 | 7/2017 | Marci et al. |
| 2017/0202518 A1 | 7/2017 | Furman et al. |
| 2017/0229037 A1 | 8/2017 | Gazzaley |
| 2017/0262943 A1 | 9/2017 | Akutagawa et al. |
| 2017/0347906 A1 | 12/2017 | Intrator |
| 2017/0352283 A1 | 12/2017 | Lau |
| 2018/0092557 A1 | 4/2018 | Bickford et al. |
| 2018/0278984 A1 | 9/2018 | Aimone |
| 2019/0021657 A1 | 1/2019 | Mohammadrezazadeh et al. |
| 2019/0082990 A1 | 3/2019 | Poltorak |
| 2019/0200888 A1 | 7/2019 | Poltorak |
| 2019/0201691 A1 | 7/2019 | Poltorak |
| 2019/0224441 A1 | 7/2019 | Poltorak |
| 2019/0246929 A1 | 8/2019 | Poltorak |
| 2019/0247662 A1 | 8/2019 | Poltorak |
| 2019/0321583 A1 | 10/2019 | Poltorak |

FOREIGN PATENT DOCUMENTS

| | | |
|---|---|---|
| WO | WO2014055932 | 4/2014 |
| WO | 2939706 | 11/2015 |
| WO | WO2019104008 | 5/2019 |

OTHER PUBLICATIONS

Stanislas Dehaene, et al., "Imaging unconscious semantic priming", Nature; vol. 395; Oct. 8, 1998; 4 pages.

John D. E. Gabrieli, et al., "The role of left prefrontal cortex in language and memory", Proc. Natl. Acad. Sci. USA, vol. 95, pp. 906-913, Feb. 1998; 8 pages.

Yang Jiang, et al., "Turning Up the Old Brain with New Tricks: Attention Training via Neurofeedback", Frontiers in Aging Neuroscience; Mar. 2017; vol. 9; Article 52; 9 pages.

Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; 3 pages.

Samat Moldakarimova, et al., "Perceptual priming leads to reduction of gamma frequency oscillations", PNAS, Mar. 23, 2010, vol. 107, No. 12; 6 pages.

M. Teplan, "Fundamentals of EEG Measurement", Measurement Science Review, vol. 2, Section 2, 2002; 11 pages.

PCT International Search Report and Written Opinion for International Appln. No. PCT/US2019/024027, Applicant HI LLC, forms PCT/ISA/210, 220 and 237 dated Aug. 19, 2019 (13 pages).

Lee, B.T., Seok, J.H., Lee., B.C, Cho, S.W., Chai, J.H., Choi, I.G., Ham, B.J., "Neural correlates of affective processing in response to sad and angry facial stimuli in patients with major depressive disorder," Prog Neuropsychopharmacol Biol Psychiatry, 32(3), 778-85 (2008.

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50,414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision making in the human brain," Nature, 431,859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10),1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

Sheline YI, Price JL, Yan Z, Mintun MA, "Resting-state functional Mri in depression unmasks increased connectivity between networks via the dorsal nexus," Proc Natl Acad Sci., 107(24), 11020-11025 (2010).

Bari A, Robbins TW, "Inhibition and impulsivity: Behavioral and neural basis of response control," Prog Neurobiol., 108:44-79 (2013).

Kagias, Konstantinos et al. "Neuronal responses to physiological stress," Frontiers in genetics, 3:222 (2012).

Clark, Ian A., et al., "First steps in using machine learning on fMRI data to predict intrusive memories of traumatic film footage", 0005-7967/ 2014 The Authors. Published by Elsevier Ltd. Behaviour Research and Therapy. This is an open access article under the CC BY license (http://creativecommons.org/licenses/by/3.0/); 10 pgs.

George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.

Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.

S.Z.K, Tan et al.,"Eternal sunshine of the neuromodulated mind: Altering fear memories through neuromodulation", Experimental Neurology 314 (2019) 9-19, 11 pages.

Zhang, Fei-Fei, et al., "Brain structure alterations in depression: Psychoradiological evidence", CNS Neurosci T 2018, John Wiley & Sons Ltd her. 2018;24:994-1003, 10 pages.

Non-Final Office Action dated Oct. 4, 2019, 26 pages.

Amendment and response filed Nov. 8, 2019, 11 pages.

Final Office Action dated Jan. 27, 2020, 21 pages.

Amendment and response filed Feb. 26, 2020, 14 pages.

Non-Final Office Action dated Mar. 23, 2020, 15 pages.

PCT International Search Report and Written Opinion for International Appln. No. PCT/US2020/025971, Applicant HI LLC, forms PCT/ISA/210, 220 and 237 dated Sep. 15, 2020 (15 pages).

Judith Amores, et al., "Promoting Relaxation Using Virtual Reality, Olfactory Interlaces and Wearable EEG," 2018 IEEE 15th International Conference on Waerable and Implantable Body Sensor Networks; Mar. 4, 2018, (4 pages).

PCT International Search Report and Written Opinion for International Appln. No. PCT/US2020/029031, Applicant HI LLC, forms PCT/ISA/210, 220 and 237 dated Sep. 2, 2020 (18 pages).

Final Office Action dated Jul. 29, 2020, 27 pages.

(56) References Cited

OTHER PUBLICATIONS

PCT International Search Report and Written Opinion for International Appln. No. PCT/US2020/034831, Applicant HI LLC, forms PCT/ISA/210 and 237 dated Feb. 8, 2021 (18 pages).

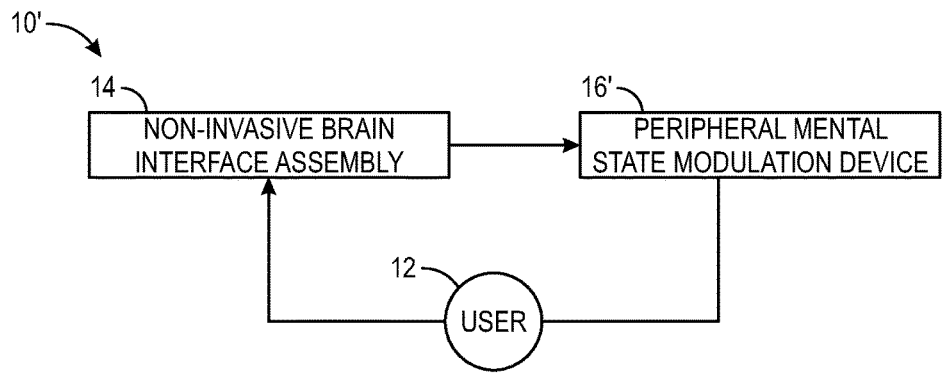
FIG. 3
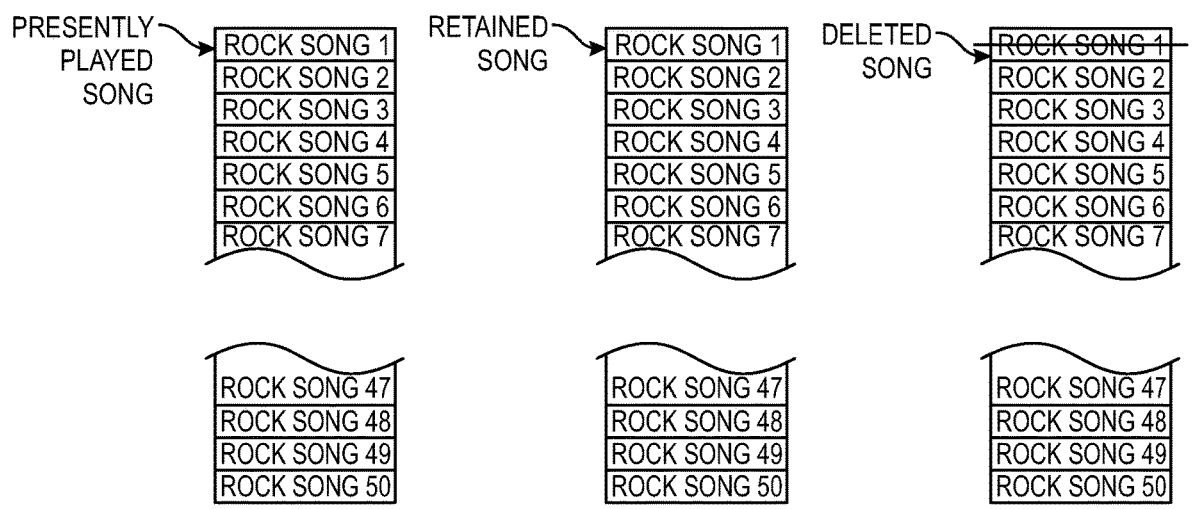
FIG. 4A  FIG. 4B  FIG. 4C

MODULATION OF MENTAL STATE OF A USER USING A NON-INVASIVE BRAIN INTERFACE SYSTEM AND METHOD

RELATED APPLICATION DATA

Pursuant to 35 U.S.C. § 119(e), this application claims the benefit of U.S. Provisional Application Ser. No. 62/829,124, filed Apr. 4, 2019, which is expressly incorporated herein by reference.

FIELD OF THE INVENTION

The present inventions relate to methods and systems for non-invasive measurements in the human body, and in particular, methods and systems related to detecting a mental state of a human.

BACKGROUND OF THE INVENTION

It is generally known that a person will experience a range of mental states through any given day. While there is universal consensus on the definition of a "mental state," for the purposes of this specification, a mental state may include emotions (e.g., joy, excitement, relaxation, surprise, anxiety, sadness, anger, disgust, contempt, fear, etc.), cognitions encompassing intellectual functions and processes (e.g., memory retrieval, focus, attention, creativity, reasoning, problem solving, decision making, comprehension and production of language, etc.), and perceptions (e.g., face perception, color perception, sound perception, etc.). Some of these mental states may be considered to be desirable, and in fact necessary for proper functioning in his or her environment, e.g., any of the cognitive states and perception states, but some of the other emotional states, e.g., anxiety, sadness, anger, disgust, contempt, fear, etc.) may be considered to be undesirable under most conditions, and counterproductive to the well-being of the person.

It is desirable that a person experience desirable mental states over undesirable mental states, not only to promote the general well-being of the person, but also to promote more objective, and thus better, decision-making. It is, of course, possible for a person to maintain a desirable mental state during long stretches of the day. For example, a person may maintain a purely cognitive state for relatively long periods when working at a job, when not tired, or not stressed out. However, when tired or stressed out, undesirable mental states may flare up. It is during these times that such person is particularly vulnerable to make bad decisions (e.g., self-harming, plotting revenge, sending an angry email or text, etc.).

It is also generally known that some of these mental states, particularly those associated with emotional states, may be subconscious, and that awareness of these subconscious mental states may lead to better mental well-being in the form of emotional mood regulation, as well as more objective decision-making. However, the conscious mind typically has only peripheral awareness, or no awareness at all, of these subconscious mental states. Thus, if a person has a negative or unhealthy mental state (e.g., anxiety) within the context of a life or work experience, such person may not be aware of it, and therefore, will be unable to take corrective actions (e.g., modifying or creating a new life or work experience) in order to alleviate or change the negative or unhealthy mental state.

It is entirely possible for the conscious mind to become aware of one's subconscious mental state. Indeed, one of the core ideas of cognitive-behavioral therapy and dialectical behavioral therapy is that if one can shape his or her mental state by consciously being aware of the mental state, this mental state, if negative, can be deliberately shaped to a more positive mental state, thereby not only promoting well-being of the individual, but also promoting better objective decision making, and more importantly, to prevent the individual from self-harming himself or herself—the issue on which dialectical behavioral therapy focuses.

However, performing behavioral therapy can be tedious, requiring the patient to track and record his or her mental state, and may thus result in patient non-compliance, or even worse, cause the patient to feel more overwhelmed, anxious, or self-critical, and thus, be counterproductive.

It is also generally known that the life/work environment of a person may significantly impact the mental state of that person, and thus, one way of modifying the mental state of a person for the better is to modify the life/work environment of such person. However, even if such person became aware of his or her normally subconscious mental state, e.g., through cognitive-behavioral therapy, dialectical behavioral therapy, or other means, such person, assuming that he or she even knew what to change in his or her life/work environment to modify the undesirable mental state, would still need to take deliberate actions to do so, which may, itself, be tedious, and thus, not worth the effort of modifying the life/work environment of the person.

As one example, there exists several computer applications for presenting different types of media to a user and tailoring that experience to the user in response to deliberate inputs from the user. For example, music streaming applications, such as Spotify®, Amazon® Music, Apple® Music, and Pandora® Radio all provide tailored music to users, while capturing the user's experience by providing the user with "heart symbol," "thumb's up symbol," "thumb's down symbol," "happy face symbol," and/or "sad face symbol," that the user can click on to provide positive or negative feedback to the current music selection, which the music streaming application would use to tailor the music to the user. However, this requires the user to actually provide input into the music streaming application, and while it generally is a fairly easy task to accomplish, requires the user to stop what he or she is doing to provide such feedback, and at times, may be impossible or even legal or impractical to do, e.g., if the user is driving a vehicle. Furthermore, the feedback provided by the user is somewhat limited in that it only reflects whether the user's subjective conscious, such as likes or dislikes of the current selection of music, and does not take into account the underlying mental state of the user.

There, thus, remains a need to automatically make a person consciously aware of his or her subconscious mental state in a normal life and work environment, so that such person may better regulate his or her emotions or make more objective decisions. There also remains a need to automatically regulate the mental state of a person to, e.g., automatically tailor the experience of a user of a media presentation system (e.g., a music streaming application) without requiring deliberate input or actions from the user.

SUMMARY OF THE INVENTION

In accordance with a first aspect of the present inventions, an entertainment system comprises a peripheral device configured for presenting content of a list of entertainment selections (e.g., a play list of songs) to a user. As one example, the peripheral device may be configured for sequentially presenting the content of the entertainment selection list to the user while the user is in a normal life and work environment, e.g., by streaming the content of the entertainment selection list to the user.

The entertainment system further comprises a non-invasive brain interface assembly (e.g., one of an optical measurement assembly and a magnetic measurement assembly) configured for detecting brain activity of the user while the peripheral device presents an entertainment selection in the entertainment selection list to the user in the normal life and work environment (e.g., by presenting content of the entertainment selection to the user or presenting a title of the entertainment selection to the user). In one embodiment, the non-invasive brain interface assembly comprises at least one detector configured for detecting energy from a brain of the user, and processing circuitry configured for identifying the brain activity in response to detecting the energy from the brain of the user. The non-invasive brain interface assembly may, e.g., comprise a head-worn unit carrying the detector(s), and an auxiliary non-head-worn unit carrying the processing circuitry.

The entertainment system further comprises at least one processor configured for determining a mental state of the user (e.g., an initial response of the user to entertainment selection presented to the user) based on the detected brain activity, and in response to the determined mental state of the user, for automatically modifying the entertainment selection list. At least a portion of the at least one processor can, e.g., be contained in the peripheral device.

In one embodiment, the determined mental state of the user is indicative of whether or not the user likes the entertainment selection presented to the user. In this case, if the determined mental state indicates that the user likes the entertainment selection presented to the user, the processor(s) may be configured for automatically modifying the entertainment selection list to retain the entertainment selection in the entertainment selection list and/or include more entertainment selections in the entertainment selection list having the same attributes as the entertainment selection that the user likes; and if the determined mental state indicates that the user dislikes the entertainment selection presented to the user, the processor(s) may be configured for automatically modifying the entertainment selection list to discard the entertainment selection from the entertainment selection list and/or include less entertainment selections in the entertainment selection list having the same attributes as the entertainment selection that the user dislikes.

In accordance with a second aspect of the present inventions, a method of entertaining a user while the user is in a normal life and work environment comprises presenting an entertainment selection from a list of entertainment selections (e.g., a play list of songs) to the user; e.g., by presenting content of the entertainment selection to the user or presenting a title of the entertainment selection to the user). The method may further comprise, e.g., sequentially presenting content of the entertainment selection list to the user, e.g., by streaming the content of the entertainment selection list to the user.

The method further comprises detecting brain activity of the user (e.g., optically or magnetically) while an entertainment selection in the entertainment selection list is presented to the user, determining a mental state of the user (e.g., an initial response of the user to entertainment selection presented to the user) based on the detected brain activity, and automatically modifying the entertainment selection list in response to the determined mental state of the user.

In one method, the determined mental state of the user is indicative of whether or not the user likes the entertainment selection presented to the user. In this case, if the determined mental state indicates that the user likes the entertainment selection presented to the user, the entertainment selection list may be automatically modified to retain the entertainment selection in the entertainment selection list and/or include more entertainment selections in the entertainment selection list having the same attributes as the entertainment selection that the user likes; and if the determined mental state indicates that the user dislikes the entertainment selection presented to the user, the entertainment selection list may be automatically modified to discard the entertainment selection from the entertainment selection list and/or include less entertainment selections in the entertainment selection list having the same attributes as the entertainment selection that the user dislikes.

In accordance with a third aspect of the present inventions, a mental state modulation system comprises a peripheral device configured for presenting life/work context to a user while the user is in normal life and work environment. The entertainment media may, e.g., comprise entertainment media (e.g., audio), which may be streaming media (e.g., music).

The mental state modulation system further comprises a non-invasive brain interface assembly (e.g., one of an optical measurement assembly and a magnetic measurement assembly) configured for detecting brain activity of the user while the user is in the normal life and work environment. In one embodiment, the non-invasive brain interface assembly comprises at least one detector configured for detecting energy from a brain of the user, and processing circuitry configured for identifying the brain activity in response to detecting the energy from the brain of the user. The non-invasive brain interface assembly may, e.g., comprise a head-worn unit carrying the detector(s), and an auxiliary non-head-worn unit carrying the processing circuitry.

The mental state modulation system further comprises at least one processor configured for determining a mental state of the user based on the detected brain activity, and in response to the determined mental state of the user, for automatically instructing the peripheral device to present the life/work context in a manner that modulates the mental state of the user. For example, if the determined mental state of the user is a negative mental state (e.g., anxiety), the mental state of the user may be modulated to promote a positive mental state (e.g., relaxation) of the user. The peripheral device may be programmed with this positive mental state. As another example, if the determined mental state of the user is an emotional state, the mental state of the user may be modulated to promote a cognitive state of the user. At least a portion of the at least one processor can, e.g., be contained in the peripheral device.

In one embodiment, the non-invasive brain interface assembly is configured for detecting the brain activity of the user while the peripheral device presents the life/work context to the user, in which case, the processor(s) may be configured for, in response to the determined mental state of the user, automatically instructing the peripheral device to modify the life/work context presented to the user in a manner that modulates the mental state of the user.

In accordance with a fourth aspect of the present inventions, a method of modulating a mental state of a user while the user is in a normal life and work environment comprises detecting brain activity of the user (e.g., optically or magnetically), determining a mental state of the user based on the detected brain activity, and automatically presenting life/work context to the user in a manner that modulates the mental state of the user in response to the determined emotional state of the user. For example, if the determined mental state of the user is a negative mental state (e.g., anxiety), the mental state of the user may be modulated to promote a positive mental state (e.g., relaxation) of the user. As another example, if the determined mental state of the user is an emotional state, the mental state of the user may be modulated to promote a cognitive state of the user. The entertainment media may, e.g., comprise entertainment media (e.g., audio), which may be streaming media (e.g., music). In one method, the brain activity of the user is detected while the life/work context to the user is presented to the user, in which case, the life/work context presented to the user may be automatically modified in a manner that modulates the mental state of the user in response to the determined mental state of the user.

In accordance with a fifth aspect of the present inventions, a mental state modulation system comprises a peripheral device configured for presenting life/work context (e.g., entertainment media (e.g., music)) to a user while the user is in a normal life and work environment.

The mental state modulation system further comprises a non-invasive brain interface assembly (e.g., one of an optical measurement assembly and a magnetic measurement assembly) configured for detecting brain activity of the user. In one embodiment, the non-invasive brain interface assembly comprises at least one detector configured for detecting energy from a brain of the user, and processing circuitry configured for identifying the brain activity in response to detecting the energy from the brain of the user. The non-invasive brain interface assembly may, e.g., comprise a head-worn unit carrying the detector(s), and an auxiliary non-head-worn unit carrying the processing circuitry.

The mental state modulation system further comprises at least one processor configured for determining a negative emotional state (e.g., one or more of anxiety, anger, disgust, fear, contempt, and sadness) of the user based on the detected brain activity, and in response to the determined negative emotional state of the user, for automatically instructing the peripheral device to present the life/work context to the user in a manner that promotes a cognitive state of the user. The peripheral device may be manually programmed with this cognitive state. At least a portion of the at least one processor can, e.g., be contained in the peripheral device.

In one embodiment, the non-invasive brain interface assembly is configured for detecting the brain activity of the user while the peripheral device presents the life/work context to the user, in which case, the processor(s) may be configured for, in response to the determined negative emotional state of the user, automatically instructing the peripheral device to modify the life/work context presented to the user in a manner that promotes the cognitive state of the user. In another embodiment, the processor(s) is further configured for determining that the user is continually in the emotional state for a certain period of time, in which case, the processor(s) may be configured for only automatically instructing the peripheral device to present the life/work context to the user only if it is determined that the user is continually in the negative emotional state for the certain period of time.

In accordance with a sixth aspect of the present inventions, a method of modulating a mental state of a user while the user is in a normal life and work environment comprises detecting brain activity of the user (e.g., optically or magnetically), determining a negative emotional state of the user (e.g., one or more of anxiety, anger, disgust, fear, contempt, and sadness) based on the detected brain activity, and automatically presenting life/work context (e.g., entertainment media (e.g., music)) to the user in a manner that promotes a cognitive state of the user. In one method, the brain activity of the user is detected while the life/work context is presented to the user, in which case, the life/work context presented to the user may be modified in a manner that promotes the cognitive state of the user in response to the determined negative emotional state of the user. Another method further comprises determining that the user is continually in the negative emotional state for a certain period of time, in which case, the life/work context may be presented to the user only if it is determined that the user is continually in the negative emotional state for the certain period of time.

In accordance with a seventh aspect of the present inventions, a mental wellness tracking system comprises a non-invasive brain interface assembly (e.g., one of an optical measurement assembly and a magnetic measurement assembly) configured for detecting brain activity of the user. In one embodiment, the non-invasive brain interface assembly comprises at least one detector configured for detecting energy from a brain of the user, and processing circuitry configured for identifying the brain activity in response to detecting the energy from the brain of the user. The non-invasive brain interface assembly may, e.g., comprise a head-worn unit carrying the detector(s), and an auxiliary non-head-worn unit carrying the processing circuitry.

The mental wellness tracking system further comprises at least one processor configured for determining a mental state of the user over the time period based on the detected brain activity, and automatically tracking the wellness of the user over the time period based on the determined mental state. The mental wellness tracking system further comprises memory configured for storing the tracked wellness of the user. The mental state may be, e.g., a negative emotional state (e.g., one or more of anxiety, anger, disgust, fear, contempt, and sadness) or a cognitive state. At least a portion of the at least one processor can, e.g., be contained in the peripheral device.

In one embodiment, tracking the wellness of the user comprises determining one of a rating of the wellness of the user, the best day of the user with respect to the determined mental state, the worst day of the user with respect to the determined mental state, the number of high points of the user with respect to the determined mental state, the number of low points of the user with respect to the determined mental state, and duration of the determined mental state. An optional embodiment of the mental wellness tracking system further comprises a peripheral device configured for presenting life/work context to the user, in which case, the processor(s) may be configured for assessing the effectiveness of the life/work context presented to the user relative to the mental state of the user determined during the time period. The peripheral device may be further configured for presenting modified life/work context to the user during a subsequent period of time based on the assessed effectiveness of the life/work context presented to the user during the time period.

In accordance with an eighth aspect of the present inventions, a method of tracking a mental wellness of a user comprises detecting brain activity of the user (e.g., optically or magnetically) over a period of time, and determining a mental state of the user over the time period based on the detected brain activity. The mental state may be, e.g., a negative emotional state (e.g., one or more of anxiety, anger, disgust, fear, contempt, and sadness) or a cognitive state.

In one method, tracking the wellness of the user comprises determining one of a rating of the wellness of the user, the best day of the user with respect to the determined mental state, the worst day of the user with respect to the determined mental state, the number of high points of the user with respect to the determined mental state, the number of low points of the user with respect to the determined mental state, and duration of the determined mental state. An optional method further comprises presenting life/work context to the user, wherein the effectiveness of the life/work context presented to the user is assessed relative to the mental state of the user determined during the time period. The optional method may further comprise presenting modified life/work context to the user during a subsequent period of time based on the assessed effectiveness of the life/work context presented to the user during the time period.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 3 is a block diagram of a non-invasive mental state modulation system constructed in accordance with one embodiment of the present inventions;

FIGS. 4A-4E are flow diagrams illustrating song play lists that are modified by the non-invasive mental state modulation system of FIG. 3;

DETAILED DESCRIPTION OF THE EMBODIMENTS

Figure 1:
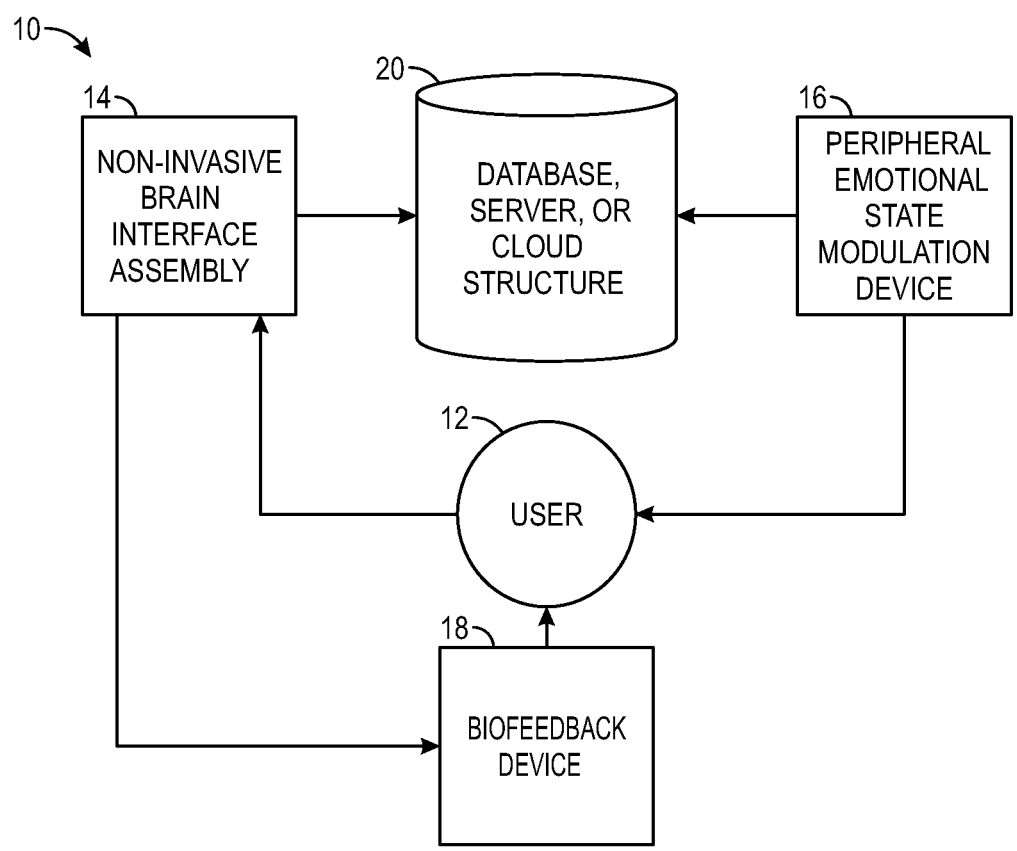
FIG. 1 is a block diagram of a non-invasive mental state awareness system constructed in accordance with one embodiment of the present inventions.

Referring now to FIG. 1, a generalized embodiment of a non-invasive mental state awareness system 10 constructed in accordance with the present inventions will be described. The non-invasive mental state awareness system 10 automatically makes a user 12 consciously aware of his or her subconscious mental state in a normal life and work environment, so that the user 12 may better regulate his or her emotions and/or make more objective decisions. For the purposes of this specification, a "normal life and work environment" is an environment that is usual and ordinary, and thus, necessitates that the user 12 be able to freely ambulate without any physical hindrance by the system 10 or other system to which the system 10 is coupled or otherwise is an adjunct. Thus, a normal life and work environment excludes a clinical setting (e.g., any setting in which a conventional magnetic resonance imaging (MRI) machine or computed tomography (CT) could potentially be used to detect neural activity from the user).

To this end, the mental state awareness system 10 comprises a non-invasive brain interface assembly 14 configured for detecting brain activity of the user 12. As will be discussed in further detail below, the brain interface assembly 14 can be optically-based, magnetically-based, or based on any other modality that enables it to non-invasively detect brain activity of the user 12 (i.e., through the intact skin and skull of the user 12), through the use of sensitive electronics, as will be described below, and is designed to be worn by the user 12. As will also be discussed in further detail below, the non-invasive brain interface assembly 14 is portable in that it can be worn by the user 12. In this manner, the mental state awareness system 10 may be conveniently used in a normal life and working environment.

The brain interface assembly 14 is also configured for determining a mental state based on the detected brain activity of the user 12, although this function can be performed by other processing components in the mental state awareness system 10, as described in further detail below. The mental state of the user 12 may include, e.g., an emotional state (e.g., joy, excitement, relaxation, surprise, anxiety, sadness, anger, disgust, contempt, fear, etc.), a cognitive state encompassing intellectual functions and processes (e.g., memory retrieval, focus, attention, creativity, reasoning, problem solving, decision making, comprehension and production of language, etc.), and a perceptive state (e.g., face perception, color perception, sound perception, etc.).

The mental state of the user 12 may be determined based on the detected brain activity in any one of a variety of manners. In one embodiment, a univariate approach in determining the mental state of the user 12 may be performed, i.e., the brain activity can be detected in a plurality (e.g., thousands) of separable cortical modules of the user 12, and the brain activity obtained from each cortical module can be analyzed separately and independently. In another embodiment, a multivariate approach in determining the mental state of the user 12 may be performed, i.e., the brain activity can be detected in a plurality (e.g., thousands) of separable cortical modules of the user 12, and the full spatial pattern of the brain activity obtained from the cortical modules can be assessed together.

Any one of a variety of models can be used to classify the mental state of the user 12, and will highly depend on the characteristics of brain activity that are input onto the models. Such characteristics of brain activity may typically be extracted from the spatiotemporal brain activity that is captured, and can include, e.g., location of signal, fine grained pattern within or across locations, amplitude of signal, timing of response to behavior, magnitude of frequency bands of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of brain activity selected to be input into the models must be considered in reference to univariate and multivariate approaches, since the univariate approach, e.g., focuses on a single location, and therefore will not take advantage of features that correlate multiple locations. The characteristics of the brain activity can be extracted from preprocessed raw data recorded during situations of patterns of thought and perception in everyday life, which are characterized by a continually changing stream of consciousness. The preprocessing of the raw data typically involves filtering the data (either in the time domain or the frequency domain) to smooth, remove noise, and separate different components of signal.

Selecting a model will be heavily dependent on whether the data is labeled or unlabeled (meaning is it known what the user is doing at the time that the brain activity is detected), as well as many other factors (e.g., is the data assumed to be normally distributed, is the data assumed relationship linear, is the data assumed relationship non-linear, etc.) Models can include, e.g., support vector machines, expectation maximization techniques, naïve-Bayesian techniques, neural networks, simple statistics (e.g., correlations), deep learning models, pattern classifiers, etc.

These models are typically initialized with some training data (meaning that a calibration routine can be performed on the user to determine what the user is doing). If no training information can be acquired, such models can be heuristically initialized based on prior knowledge, and the models can be iteratively optimized with the expectation that optimization will settle to some optimal maximum or minimum solution. Once it is known what the user is doing, the proper characteristics of the neural activity and proper models can be queried. The models may be layered or staged, so that, e.g., a first model focuses on pre-processing data (e.g., filtering), the next model focuses on clustering the pre-processed data to separate certain features that may be recognized to correlate with a known activity performed by the user, and then the next model can query a separate model to determine the mental state based on that user activity.

As will be described in further detail below, the training data or prior knowledge of the user may be obtained by providing known life/work context to the user. Altogether, the models can be used to track mental state and perception under natural or quasi-natural (i.e., in response to providing known life/work context to the user) and dynamic conditions taking in the time-course of averaged activity and determining the mental state of the user based on constant or spontaneous fluctuations in the characteristics of the brain activity extracted from the data.

A set of data models that have already been proven, for example in a laboratory setting, can be initially uploaded to the mental state awareness system 10, which system will then use the uploaded models to determine the mental state of the user. Optionally, the mental state awareness system 10 may collect data during actual use with the user, which can then be downloaded and analyzed in a separate server, for example in a laboratory setting, to create new or updated models. Software upgrades, which may include the new or updated models, can be uploaded to the mental state awareness system 10 to provide new or updated data modelling and data collection.

Further details regarding determining the mental state of a person based on detected brain activity can be found in a variety of peer-reviewed publications. See, e.g., Lee, B. T., Seok, J. H., Lee., B. C, Cho, S. W., Chai, J. H., Choi, I. G., Ham, B. J., "Neural correlates of affective processing in response to sad and angry facial stimuli in patients with major depressive disorder," *Prog Neuropsychopharmacol Biol Psychiatry,* 32(3), 778-85 (2008); A. C. Felix-Ortiz, A. C., Burgos-Robles, A., Bhagat, N. D., Leppla, C. A., Tye, K. M., "Bidirectional modulation of anxiety-related and social behaviors by amygdala projections to the medial prefrontal cortex," *Neuroscience* 321, 197-209 (2016); Beauregard, M., Levesque, J. & Bourgouin, P., "Neural correlates of conscious self-regulation of emotion," *J. Neurosci.* (2001): 21, RC165; Phan, K. L., Wager, T., Taylor, S. F. & Liberzon, I., "Functional neuroanatomy of emotion: a meta-analysis of emotion activation studies in PET and fMRI," *Neuroimage,* 16, 331-348 (2002); Canli, T. & Amin, Z., "Neuroimaging of emotion and personality: scientific evidence and ethical considerations," *Brain Cogn.,* 50, 414-431 (2002), McCloskey, M. S., Phan, K. L. & Coccaro, E. F., "Neuroimaging and personality disorders," *Curr. Psychiatry Rep.,* 7, 65-72 (2005); Heekeren, H. R., Marrett, S., Bandettini, P. A. & Ungerleider, L. G., "A general mechanism for perceptual decision-making in the human brain," *Nature,* 431, 859-862 (2004); Shin L M, Rauch S L, Pitman R K. Amygdala, Medial Prefrontal Cortex, and Hippocampal Function in PTSD, *Ann N Y Acad Sci.,* 1071(1) (2006); Lis E, Greenfield B, Henry M, Guile J M, Dougherty G., "Neuroimaging and genetics of borderline personality disorder: a review," *J Psychiatry Neurosci.,* 32(3), 162-173 (2007); Etkin A, Wager T D, "Functional neuroimaging of anxiety: a meta-analysis of emotional processing in PTSD, social anxiety disorder, and specific phobia," *Am J Psychiatry,* 164(10),1476-1488 (2007); Etkin A. Functional Neuroimaging of Major Depressive Disorder: A Meta-Analysis and New Integration of Baseline Activation and Neural Response Data, *Am J Psychiatry,* 169(7), 693-703 (2012); Sheline Y I, Price J L, Yan Z, Mintun M A, "Resting-state functional MRI in depression unmasks increased connectivity between networks via the dorsal nexus, *Proc Natl Acad Sci.,* 107(24), 11020-11025 (2010); Bari A, Robbins T W, "Inhibition and impulsivity: Behavioral and neural basis of response control," *Prog Neurobiol.*, 108:44-79 (2013); Kagias, Konstantinos et al. "Neuronal responses to physiological stress," Frontiers in genetics, 3:222 (2012).

The mental state awareness system 10 further comprises an optional peripheral life/work context device 16 (e.g., a Smartphone, tablet computer, or the like) configured for incorporating known life/work context (e.g., GPS tracking, calendar scheduling, means for listening to music, means for listening to a lecture, means for learning a language, means for engaging in video conversations with others located in remote locations, etc.) to promote, adjust and/or calibrate the experience of the user 12.

For example, based on this known life/work context provided to the user 12 via the peripheral device 16, the quasi-natural conditions that are contributed to or promoting the actual mental state of the user 12 can be known or better assessed to more accurately determine this mental state.

As another example, the peripheral device 16 may provide the known life/work context to the user 12 to automatically promote, adjust, regulate, and/or calibrate the mental state of the user, e.g., anxiety, fear, alertness. For example, if the determined mental state of the user 12 is anxiety, then the peripheral device 16 may change a music selection to a more soothing melody.

The experience of the user 12 can also be individually programmed using a manual selection or manual input on the peripheral device 16 by the user 12. For example, a variety of individual experiences, such as reading, meditation, taking a nap, watching a television program, watching a live theater or musical performance, or the option for programming any other type of individual experience, can be available from the peripheral device 16 through a menu of selectable options in order to promote, adjust, regulate and/or calibrate the mental state of the user 12. Such experiences can be selected or individually programed by the user 12, and can be made available through the graphical user interface of the peripheral device 16 though a button, tab, or icon, e.g., through the use of a radio button or similar selectable options, representing one of a set of options of individual experiences.

The mental state awareness system 10 further comprises an optional biofeedback device 18 configured for automatically providing biofeedback to the user 12 indicative of the mental state determined by the brain interface assembly 14. In the preferred embodiment, the optional biofeedback device 18 is configured for providing/directing vibrational (or haptic) signals indicative of the determined mental state of the user 12 through peripheral somatosensation, e.g., to areas of the user's 12 skin, e.g., arm, wrist, hand, finger, etc., to provide the user 12 convenient awareness recognition of the determined mental state. The biofeedback device 18 may encode different messages by how the vibrations are constructed or modulated in amplitude or frequency. In one embodiment, the vibrations encode speech, e.g., conversations or speech envelopes, or encode speech at a word level, e.g., single vowel, single word, or a combination of single words and vowels. In another embodiment, the vibration modalities may be encoded to mental state type, level, urgency, or other user-relevant information.

As such, the optional biofeedback device 18 can serve as brain input through the peripheral nervous (PNS) or sympathetic nervous system (SNS), thereby closing the loop that connects the user's 12 subconscious mental state via brain interfaces by the brain interface assembly 14 to the user's 12 conscious awareness of such mental state. In alternative embodiments, the biofeedback device 18 may be configured for providing/directing audio or visual feedback to the user 12 that may be encoded to signal urgency, levels of mental states, or other user-relevant information, which likewise serves as brain input through the audio or visual nervous system, thereby closing the loop that connects the user's 12 subconscious mental state to the user's 12 conscious awareness of such mental state.

The mental state awareness system 10 also optionally comprises a database, server, or cloud structure 20 configured for tracking the brain activity of the user 12. For example, the database, server, or cloud structure 20 may be configured to collect raw data (e.g., brain activity data) generated by the brain interface assembly 14. Furthermore, the database, server, or cloud structure 20 (independently of or in conjunction with the mental state determination functions of the brain interface assembly 14) may be configured for performing a data analysis of the raw data in order to determine the mental state of the user 12.

For example, if the raw data obtained by the user 12 is being anonymized and stored in the database, server, or cloud structure 20, the data models can be pooled across various users, which deep learning algorithms would benefit from. The database, server, or cloud structure 20 may be configured for performing cross-correlation analysis of the signal data analysis in order to reduce the pool size of the database and focus subject averaged data to a pool that is similar to the user. Most likely, each user will have a portion of their model optimized to them, but then another portion takes advantage of patterns extracted from a larger pool of users. It should also be appreciated that each user may perform any variety of an infinite number of activities. Thus, even if a user is properly calibrated, such calibration will only be for a small set of infinite possibilities. Generalizing models may comprise various variabilities and optimizing may be difficult. However, by building a large user database on the database, server, or cloud structure 20, a data analysis pipeline connected to such database, server, or cloud structure 20 can preprocess data (clean it up), extract all different kinds of features, and then apply an appropriate data model, to overcome this issue. The brain activity of the user 12 may be tracked with additional life/work context to acquire meta data in depth assessment of awareness and behavior modulation patterns of the user 12. Although, all of the tracked data analysis has been described as being performed by the database, server, or cloud structure 20, it should be appreciated that at least a portion of the tracked data analysis functionality may be incorporated in the peripheral device 16, with the caveat that it is preferred that the tracking of the brain activity between a pool of users be performed by the database, server, or cloud structure 20.

Figure 2:
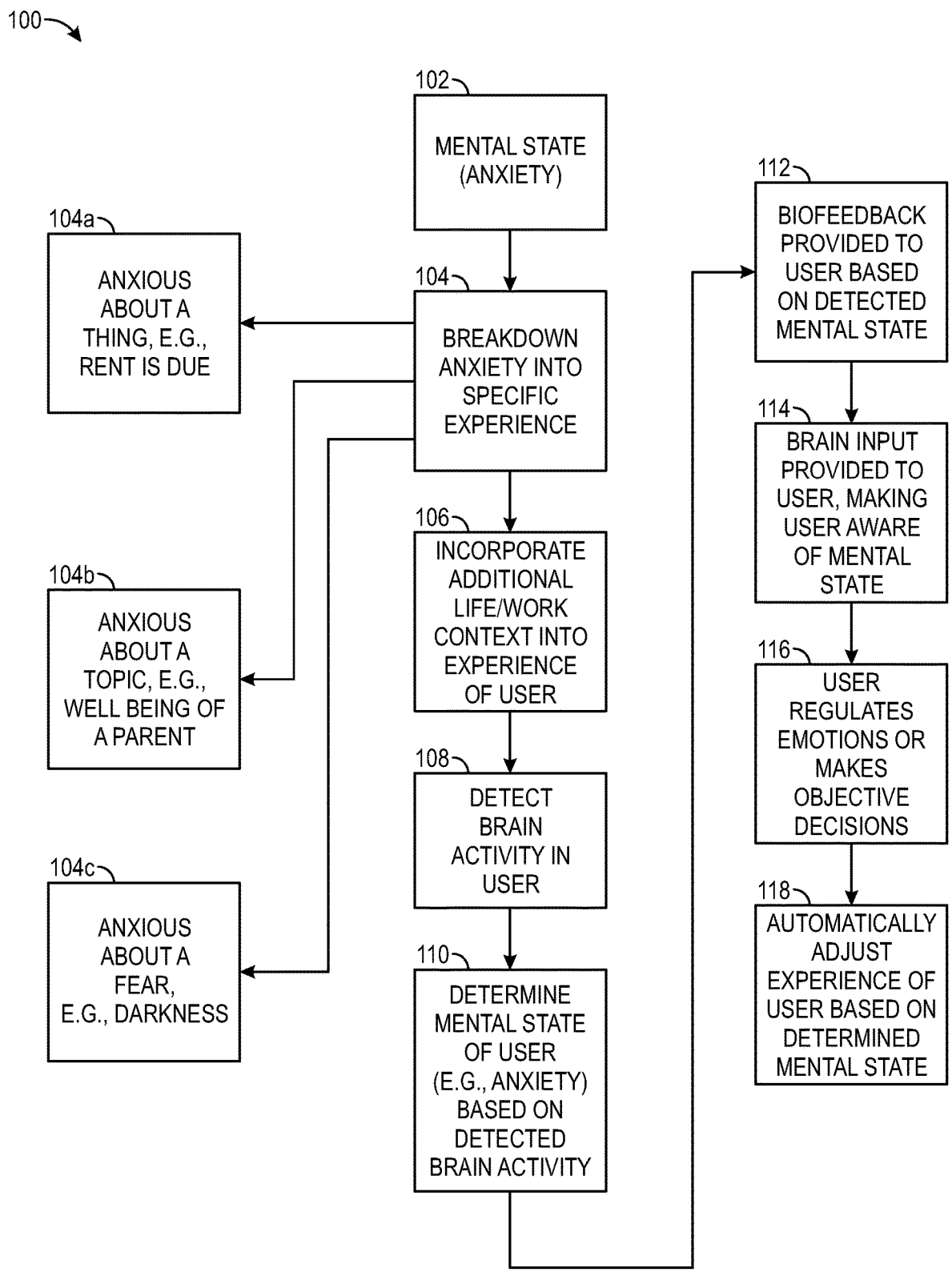
FIG. 2 is a flow diagram illustrating one method of operating the non-invasive mental state awareness system of FIG. 1.

Having described the structure, function, and application of data models of the mental state awareness system 10, one method 100 of operating the mental state awareness system 10 will now be described with reference to FIG. 2.

Initially, the user 12 may have a subconscious mental state (block 102). Such mental state may be, e.g., anxiety, although the user 12 may have other mental states as set forth above. The anxiety of the user 12 may be broken down into a specific experience (block 104), e.g., anxiety about a thing (block 104a), e.g., rent, mortgage, or credit card payment is due, anxiety about a topic (block 104b), e.g., concerned over the well-being of a parent, being interviewed, presenting or acting in front of an audience, or anxiety about fear (block 104c), e.g., fear of darkness in unfamiliar spaces, fear of aircraft travel, fear of ocean liner travel, fear of heights. The peripheral device 16 may incorporate additional life/work context into the experience of the user 12 (e.g., GPS tracking, calendar scheduling, means for listening to music, means for listening to a lecture, means for learning a language, means for engaging in video conversations with others located in remote locations, etc.) (block 106). It should be appreciated that, although the additional life/work context is illustrated as being provided to the user 12 after or during the initial experience that results in the mental state, the additional life/work context can be provided to the user 12 at any time during the method 100.

The brain interface assembly 14 detects the brain activity of the user 12 (block 108). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then determines the mental state of the user 12 (in this case, anxiety) based on the detected brain activity (block 110).

The biofeedback device 18 then provides biofeedback to the user 12 indicative of the determined mental state of the user 12 caused by any one of the experiences (block 112). For example, the biofeedback device 18 may provide/direct vibrational signals to the user 12 indicative of the determined mental state of the user 12 through peripheral somatosensation, e.g., vibrational signals encoded with one or more messages, or alternatively, may provide/direct audio or visual signals to the user 12 indicative of the determined mental state of the user 12. Thus, input is provided to the brain of the user 12 to make the user 12 aware of his or her mental state, thereby closing the loop on the experience 108 (block 114). As such, the user 12 may regulate, adjust, and/or calibrate his or her emotions or make more objective decisions (block 116). Furthermore, the peripheral device 16 may automatically regulate, adjust and/or calibrate the experience of the user 12 based on the determined mental state of the user 12 by, e.g., playing soothing music (block 118).

Referring now to FIG. 3, a generalized embodiment of a non-invasive mental state modulation system 10' constructed in accordance with the present inventions will be described. The mental state modulation system 10' differs from the non-invasive mental state awareness system 10 described above in that the mental state modulation system 10' does not comprise a biofeedback device 18 that closes the loop between the brain interface assembly 14 and the user 12 to automatically make the user 12 consciously aware of his or her subconscious mental state. Instead, the mental state modulation system 10' automatically regulates the mental state of the user 12 without requiring deliberate input or actions from the user 12 after the determination of the mental state, i.e., the mental state modulation system 10' transparently and seamlessly regulates the mental state of the user 12, perhaps without even the conscious knowledge of the user 12.

To this end, the mental state modulation system 10' comprises the non-invasive brain interface assembly 14 configured for detecting brain activity of the user 12. Although not illustrated, the mental state modulation system 10' may optionally comprise the database, server, or cloud structure 20 (shown in FIG. 1) configured for tracking the brain activity of the user 12. The non-invasive brain interface assembly 14 and database, server, or cloud structure 20 may function in the same manner as described above with respect to the mental state awareness system 10.

The mental state modulation system 10' comprises a peripheral mental state modulation device 16' (e.g., a Smartphone, tablet computer, or the like) configured for, in response to the determined mental state of the user 12, automatically presenting life/work context to the user 12 in a manner that modulates the mental state of the user 12. For example, if the mental state of the user 12 is determined to be a negative mental state, typically a negative emotional state, such as, e.g., anxiety, sadness, anger, disgust, contempt, fear, etc., the mental state of the user 12 may be modulated to promote a positive mental state of the user 12. In one embodiment, such positive mental state may be a positive emotional state, such as, e.g., joy, excitement, relaxation, surprise, etc.

One or more negative mental states and/or one or more positive mental states can be programmed into the peripheral device 16', such that the non-invasive brain interface assembly 14 may focus on the programmed negative state(s) when analyzing the brain activity of the user 12, and the peripheral device 16' presents the life/work context to the user 12 in a manner that promotes the programmed positive mental state(s) in the user 12. For example, anxiety and relaxation may be programmed into the peripheral device 16', such that the non-invasive brain interface assembly focuses on the mental state of anxiety when analyzing the brain activity of the user 12, and the peripheral device 16' presents the life/work context to the user 12 in a manner that promotes the mental state of relaxation in the user 12. In one embodiment, the opposing negative and positive mental state pairs can be assumed, such that an opposing negative state/positive state pair can be programmed into the peripheral device 16'. For example, it is known that sadness-joy, anxiety-relaxation, excitement-disgust, etc., are complementary mental state pairs, and thus, they can be programmed as pairs into the peripheral device 16'.

In another embodiment, such positive mental state may be a cognitive state encompassing intellectual functions and processes, such as, e.g., memory retrieval, focus, attention, creativity, reasoning, problem solving, decision making, comprehension and production of language, etc. The goal of this embodiment is to maintain the user 12 within the cognitive state (where better objective decision-making can be made and/or maximize production of the user 12 within a work environment) while preventing the user 12 from slipping into a negative and counterproductive emotional state. It should be appreciated that maintaining the user 12 within a cognitive state does not mean that the user 12 will be devoid of any emotion, but rather such user 12 will tend to use transient emotions as information, and will not dwell on any particular negative emotion. As such, the peripheral device 16' may only modulate the mental state of the user 12 if the non-invasive brain interface assembly 14 determines that the user 12 is continually (either continuously or intermittently) in a negative emotional state for a certain period of time. For example, only after it has been determined that the user 12 is angry for a period of greater than 15 minutes, the peripheral device 16' may then modulate the mental state of the user 12 to promote a cognitive mental state of the user 12.

In another embodiment, the non-invasive brain interface assembly 14 is configured for detecting the brain activity of the user 12 while the peripheral device 16' provides the life/work context to the user 12. In this case, the peripheral device 16' will be configured for modifying the life/work context presented to the user 12 in a manner that modulates the mental state of the user 12. This embodiment lends itself well to entertainment systems. For example, the life/work context presented by the peripheral device 16' to the user 12 may comprise entertainment media, which may be streamed. Such entertainment media may comprise audio, such as music, which may be performed by such services as Spotify®, Amazon® Music, Apple® Music, Pandora® Radio, etc., although other types of entertainment media are contemplated, including video, which may be performed by such services at Youtube®, Netflix®, Hulu®, Amazon® Video, etc. Thus, the peripheral device 16' may automatically modify the entertainment media to promote the positive mental state of the user 12.

In one example, the entertainment media comprises a plurality of different entertainment selections, in which case, the peripheral device 16' may be configured for automatically modifying the entertainment media by presenting the content of a list of entertainment selections (i.e., playing the list of entertainment selections) to the user 12 that promote the positive mental state of the user 12. The content of the entertainment selection list may be sequentially presented to the user, e.g., via media streaming. The peripheral device 16' may also be configured for presenting the titles of the entertainment selections in at least a portion of the entertainment selection list to provide the user 12 with a complete or partial view of the entertainment selection list. The list of entertainment selections may be pre-generated (i.e., before the first entertainment selection is presented to the user 12) or may be dynamically generated, e.g., entertainment selections may be incorporated into the list after the first entertainment selection is presented to the user 12. In the context of music, the peripheral device 16' may be configured for presenting the content of a play list of songs (i.e., playing the songs) to the user 12, as illustrated in FIG. 4A. The song play list may, e.g., correspond to a particular genre of music (e.g., Rock, Country, Jazz, etc.), and in this case, a list of 50 Rock songs. In an alternative embodiment, the titles of the songs may be presented in a complete or partial view showing the list of entertainment selections.

The non-invasive brain interface assembly 14 may be configured for detecting brain activity of the user 12 while the peripheral device 16' plays a song in the song play list to the user 12, and the peripheral device 16' may be further configured for determining the mental state of the user 12 (e.g., the initial response of the user 12 to the song) based on the detected brain activity, e.g., a mental state that is indicative of whether or not the user 12 likes the song played to the user 12. In an alternative embodiment, the peripheral device 16' may be configured for determining the mental state of the user 12 based on the detected brain activity when a title of the song is presented to the user 12, although it is believed that playing the song to the user 12 will evoke a more visceral reaction from the user 12, and thus, providing a more accurate of indication of the reaction of the user 12 to the song (e.g., whether the user 12 likes the song). In any event, the peripheral device 16' is further configured for automatically modifying this song play list based on the determined mental state of the user 12.

Figure 4D:
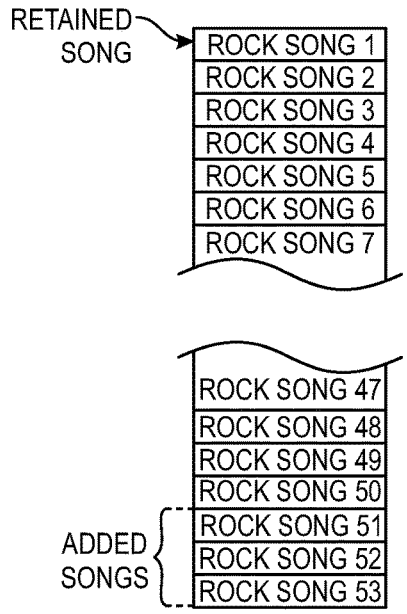
Figure 4E:
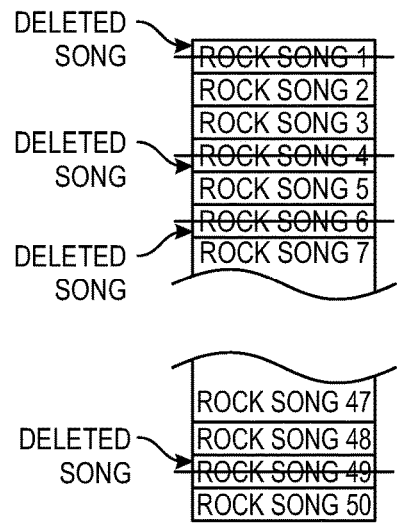

For example, if the determined mental state indicates that the user 12 likes the song, the peripheral device 16' may be configured for automatically modifying the song play list to retain the song in the song play list (in this case Rock Song 1), as illustrated in FIG. 4B, and if the determined mental state indicates that the user 12 dislikes the song, the peripheral device 16' may be configured for automatically modifying the song play list to discard the song from the song play list (in this case Rock Song 1), as illustrated in FIG. 4C. Furthermore, if the determined mental state indicates that the user 12 likes the song, the peripheral device 16' may not only be configured for retaining the song in the song play list, the peripheral device 16' may be configured for including more songs in the song play list having the same attributes as the song that the user 12 likes (in this case, Rock Songs 51-53), as illustrated in FIG. 4D, and if the determined mental state indicates that the user 12 dislikes the song, the peripheral device 16' may not only be configured for discarding the song from the song play list, the peripheral device 16' may be configured for including less songs in the song play list having the same attributes as the song that the user 12 dislikes (in this case Rock Songs 4, 6, and 49), as illustrated in FIG. 4E.

The experience of the user 12 can also be individually programmed using a manual selection or manual input on the peripheral device 16' by the user 12. For example, a variety of individual experiences, such as reading, meditation, taking a nap, watching a television program, watching a live theater or musical performance, or the option for programming any other type of individual experience, can be available from the peripheral device 16' through a menu of selectable options in order to promote, adjust, regulate and/or calibrate the mental state of the user 12. Such experiences can be selected or individually programed by the user 12, and can be made available through the graphical user interface of the peripheral device 16' though a button, tab, or icon, e.g., through the use of a radio button or similar selectable options, representing one of a set of options of individual experiences.

It should be appreciated that although the peripheral device 16' has been described as performing the processing necessary for modifying the life/work context presented to the user in a manner that modulates the mental state of the user 12, such processing can be performed external to the peripheral device 16', e.g., in the non-invasive brain interface assembly 14.

Figure 5:
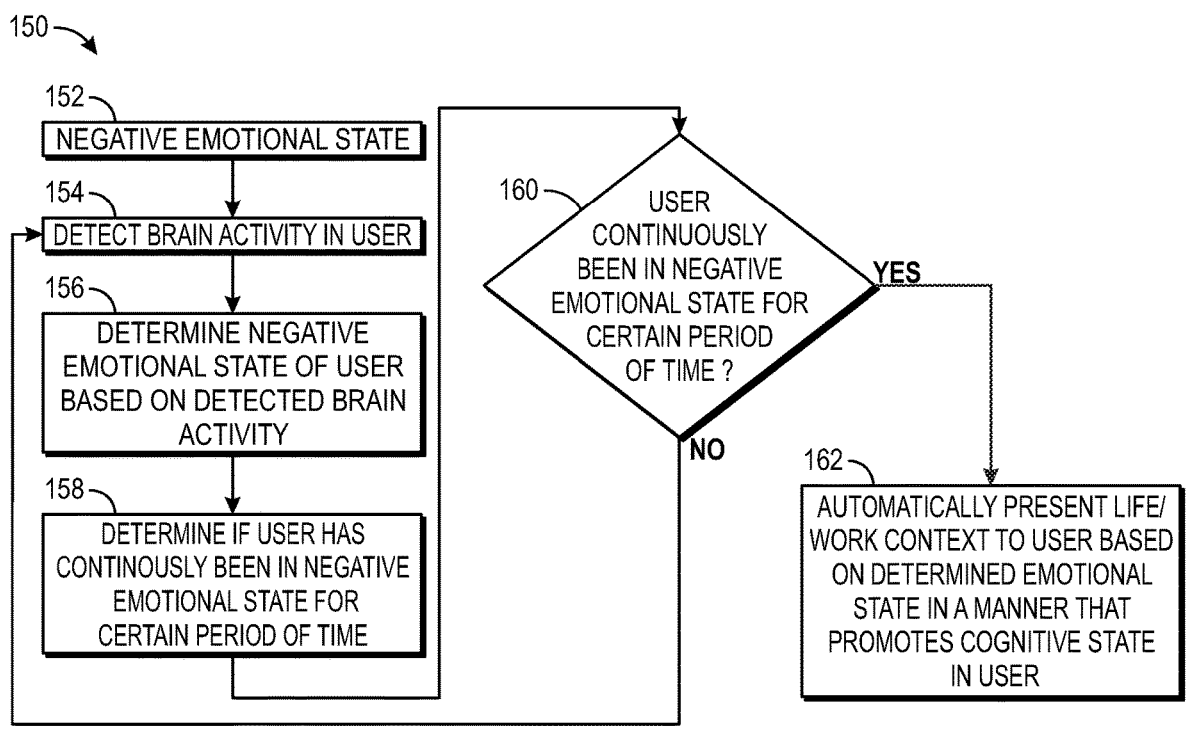
FIG. 5 is a flow diagram illustrating one method of operating the non-invasive mental state modulation system of FIG. 3.

Having described the structure, function, and application of data models of the mental state modulation system 10', one method 150 of operating the mental state modulation system 10' will now be described with reference to FIG. 5.

Initially, the user 12 may have a mental state, which may be conscious or subconscious (block 152). In the illustrated method, the mental state is a negative emotional state (e.g., anxiety, anger, disgust, fear, contempt, and sadness), although other mental states are contemplated as set forth above. The brain interface assembly 14 detects the brain activity of the user 12 (block 154). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then determines the negative emotional state of the user 12 based on the detected brain activity (block 156).

Next, the peripheral device 16' determines whether the user 12 has been continually in the negative emotional state for a certain period of time (block 158). If the user 12 is determined to be continually in the negative emotional state for the certain period of time (block 160), the peripheral device 16' automatically presents life/work context (e.g., streaming entertainment media, such as audio (e.g., music)) to the user 12 based on the determined mental state of the user 12 in a manner that modulates the mental state of the user 12 (block 162). In the illustrated embodiment, the mental state of the user 12 is modulated to promote a positive state (e.g., a cognitive state), although the promotion of other mental states is also contemplated as set forth above. If the user 12 is determined to not be continually in the determined emotional state for the certain period of time (block 160), the peripheral device 16' does not automatically presents life/work context to the user 12 in a manner that modulates the mental state of the user 12, but rather returns to block 154.

Figure 6:
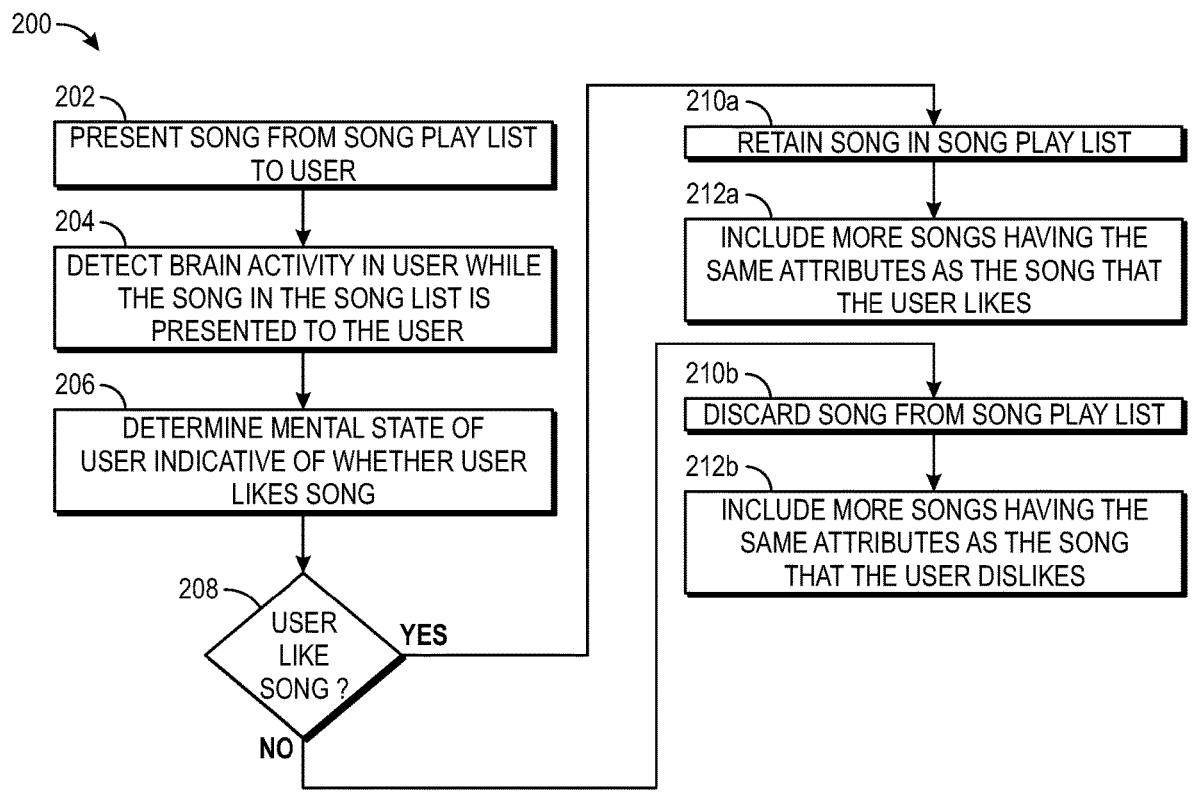
FIG. 6 is a flow diagram illustrating another method of operating the non-invasive mental state modulation system of FIG. 3.

Another method 200 of operating the mental state modulation system 10' will now be described with reference to FIG. 6. The method 200 differs from method 150 in that the brain interface assembly 14 detects the brain activity of the user 12 while the peripheral device 16' presents the life/work context to the user 12, and the peripheral device 16' modify the life/work context presented to the user 12 in a manner that modulates the mental state of the user 12. This method 200 lends itself well to the presentation of entertainment media to a user, and will be described in this context.

Initially, the peripheral device 16' presents an entertainment selection from a list of entertainment selections to the user 12 (e.g., streaming) (block 202). In the illustrated method, the list of entertainment selections is a song play list, although other types of entertainment selection lists can be used, e.g., a list of videos. The brain interface assembly 14 detects the brain activity of the user 12 while a song in the song play list is presented to the user 12 (block 204). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then determines, based on the detected brain activity, a mental state of the user 12 indicative of whether or not the user 12 likes the song presented to the user 12 (block 206). As one example, the mental state of the user 12 detected by the brain interface assembly 14 may be an initial response of the user 12 to the song presented to the user 12.

If the determined mental state indicates that the user 12 likes the song presented to the user 12 (step 208), the peripheral device 16' automatically modifies the song play list to retain the song in the song list (step 210a), and to include more songs having the same attributes as the song that the user 12 likes (step 212a). In contrast, if the determined mental state indicates that the user 12 dislikes the song presented to the user 12 (step 208), the peripheral device 16' automatically modifies the song play list to discard the song from the song play list (step 210b), and to include less songs having the same attributes as the song that the user 12 dislikes (step 212b).

Figure 7:
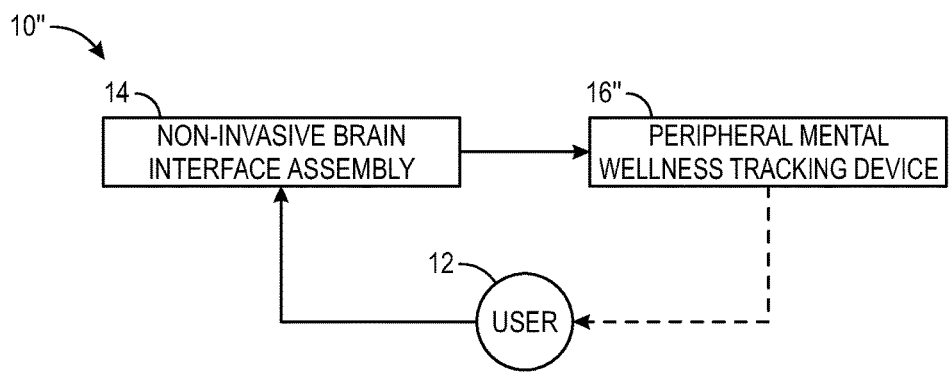
FIG. 7 is a block diagram of a non-invasive mental wellness tracking system constructed in accordance with one embodiment of the present inventions.

Referring now to FIG. 7, a generalized embodiment of a non-invasive mental wellness tracking system 10" constructed in accordance with the present inventions will be described. The mental wellness tracking system 10" differs from the non-invasive mental state modulation system 10' described above in that the mental wellness tracking system 10" automatically tracks the mental wellness of the user 12, with the optional functionality of modulating the mental state of the user 12, such that the effectiveness of such mental state modulation can be monitored and changed if necessary.

To this end, the mental wellness tracking system 10" comprises the non-invasive brain interface assembly 14 configured for detecting brain activity of the user 12. Although not illustrated, the mental wellness tracking system 10" may optionally comprise the database, server, or cloud structure 20 (shown in FIG. 1). The non-invasive brain interface assembly 14 and database, server, or cloud structure 20 may function in the same manner as described above with respect to the mental state awareness system 10.

The mental wellness tracking system 10" further comprises a peripheral mental wellness tracking device 16" (e.g., a Smartphone, tablet computer, or the like) configured for automatically tracking the mental wellness of the user 12 over a period of time. Optionally, the optional database, server, or cloud structure 20 may be configured for automatically tracking the mental wellness of the user 12 over the period of time. The peripheral device 16" or optionally the database, server, or cloud structure 20 may be configured for storing the tracked mental awareness of the user 12 for subsequent recall. As shown by the dashed arrow line illustrated in FIG. 7, the peripheral device 16" may also be optionally configured for automatically presenting life/work context to the user 12 in a manner that modulates the mental state of the user 12 in the same manner described above with respect to the peripheral mental state modulation device 16'.

In one embodiment, the mental state of the user 12 that is determined over the period of time is a negative emotional state of the user 12 (e.g., one or more of anxiety, anger, disgust, fear, contempt, and sadness). In another embodiment, the mental state of the user 12 that is determined over the period of time is a cognitive state of the user 12. In either case, tracking the mental wellness of the user 12 over the period of time (e.g., a week) by the peripheral device 16" (or optionally the database, server, or cloud structure 20) may, e.g., comprise determining one of a rating of the wellness of the user, the best day of the user with respect to the determined mental state, the worst day of the user with respect to the determined mental state, the number of high points of the user with respect to the determined mental state, the number of low points of the user with respect to the determined mental state, and the duration or durations of the determined mental state.

If the peripheral device 16" is configured for optionally presenting life/work context to the user 12 during the period of time in a manner that modulates the mental state of the user 12, information related to the tracked wellness of the user 12 over the period of time may be analyzed to assess the effectiveness of the life/work context relative to the determined mental state. In this case, the peripheral device 16" is optionally configured for modifying the life/work context to be presented to the user 12 to improve its effectiveness with respect to the determined mental state, and then presenting such modified life/work context to the user 12 during the subsequent time period. For example, if the determined mental state of the user 12 is a negative emotional state, the life/work context presented to the user 12 may be modified to improve its effectiveness in promoting a more positive emotional state. If the determined mental state of the user 12 is a cognitive state, the life/work context presented to the user 12 may be modified to improve its effectiveness in promoting such cognitive mental state.

Figure 8:
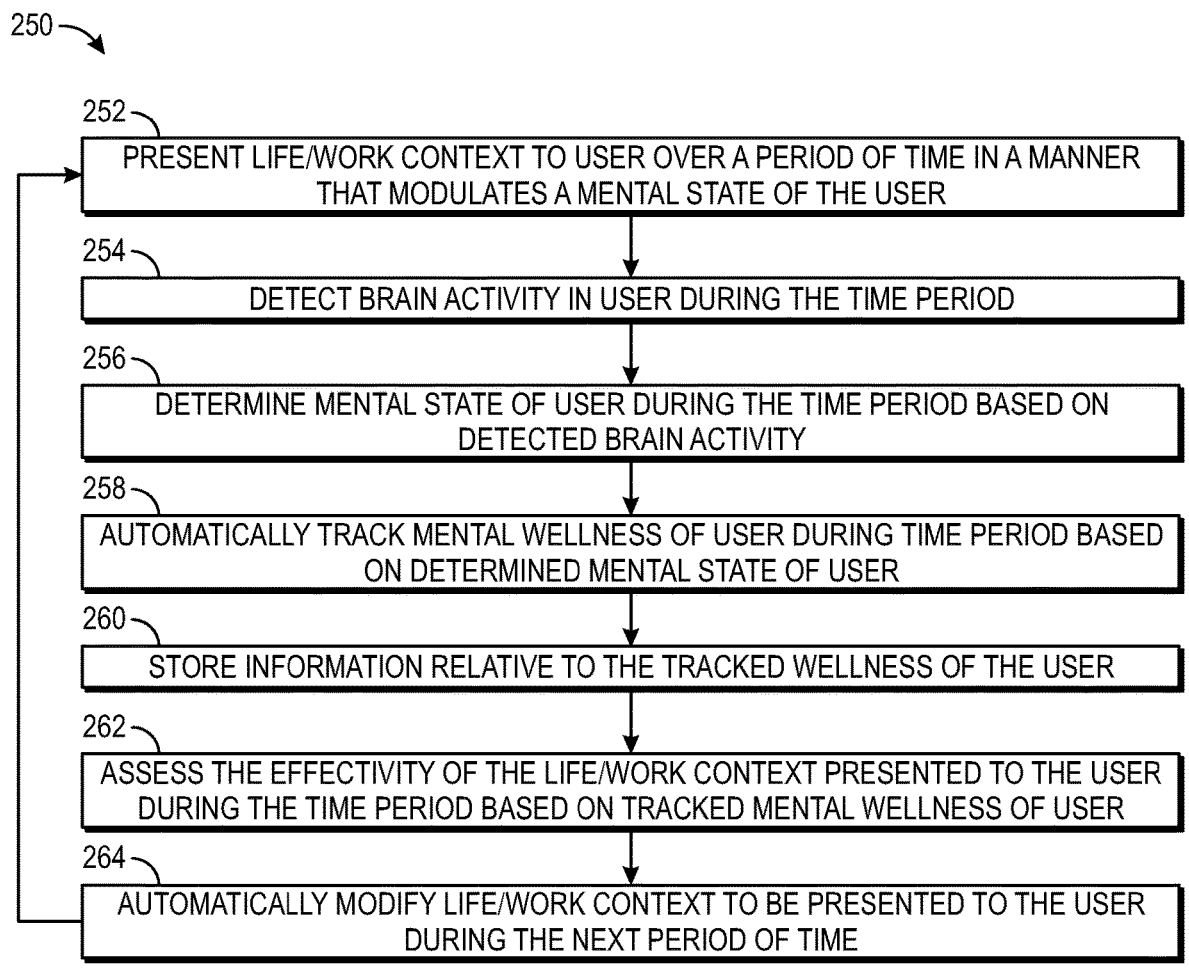
FIG. 8 is a flow diagram illustrating one method of operating the non-invasive mental wellness tracking system of FIG. 7.

Having described the structure, function, and application of data models of the mental state wellness tracking system 10", one method 250 of operating the mental state wellness tracking system 10" will now be described with reference to FIG. 8. It should be noted that the method 250 is described as tracking the mental wellness of the user 12 for the purpose of improving life/work context as provided by the peripheral device 16" to the user 12, although other alternative methods may simply track the mental wellness of the user 12 for the purpose of making the user 12 or a third person aware of the mental wellness of the user 12.

The peripheral device 16" first optionally presents life/work context to the user 12 in a manner that modulates the mental state of the user 12 over a period of time (e.g., a week) (block 252). In the illustrated method, the peripheral device 16" presents life/work context to the user 12 in a manner that promotes a positive mental state of the user 12

(e.g., a positive emotional state or a cognitive state). The life/work context may be continuously or intermittently presented to the user 12 over the time period. The brain interface assembly 14 detects the brain activity of the user 12 during the time period (block 254). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then automatically determines the mental state of the user 12 (e.g., the negative emotional state, positive emotional state, and/or the cognitive state) during the time period based on the detected brain activity (block 256).

The peripheral device 16 (or alternatively, the database, server, or cloud structure 20) automatically tracks the mental wellness of the user 12 during the time period based on the mental state of the user 12 determined during the period, e.g., the rating of the wellness of the user, the best day of the user with respect to the determined mental state, the worst day of the user with respect to the determined mental state, the number of high points of the user with respect to the determined mental state, the number of low points of the user with respect to the determined mental state, and duration of the determined mental state (block 258). The information related to the tracked wellness of the user 12 is then stored in memory (e.g., in the peripheral device 16" or database, server, or cloud structure 20) (block 260).

Next, the peripheral device 16 (or alternatively, the database, server, or cloud structure 20) assesses the effectivity of the life/work context presented to the user 12 during the time period (block 262), and automatically modifies the life/work context to be presented to the user 12 during the next time period based on the assessed effectivity of the life/work context presented to the user 12 during the current time period (block 264). For example, if the determined mental state of the user 12 is a negative emotional state, the life/work context presented to the user 12 may be modified to improve its effectiveness in promoting a more positive emotional state. If the determined mental state of the user 12 is a cognitive state, the life/work context presented to the user 12 may be modified to improve its effectiveness in promoting such cognitive mental state. The method 250 then returns to block 252 and repeats.

Figure 9:
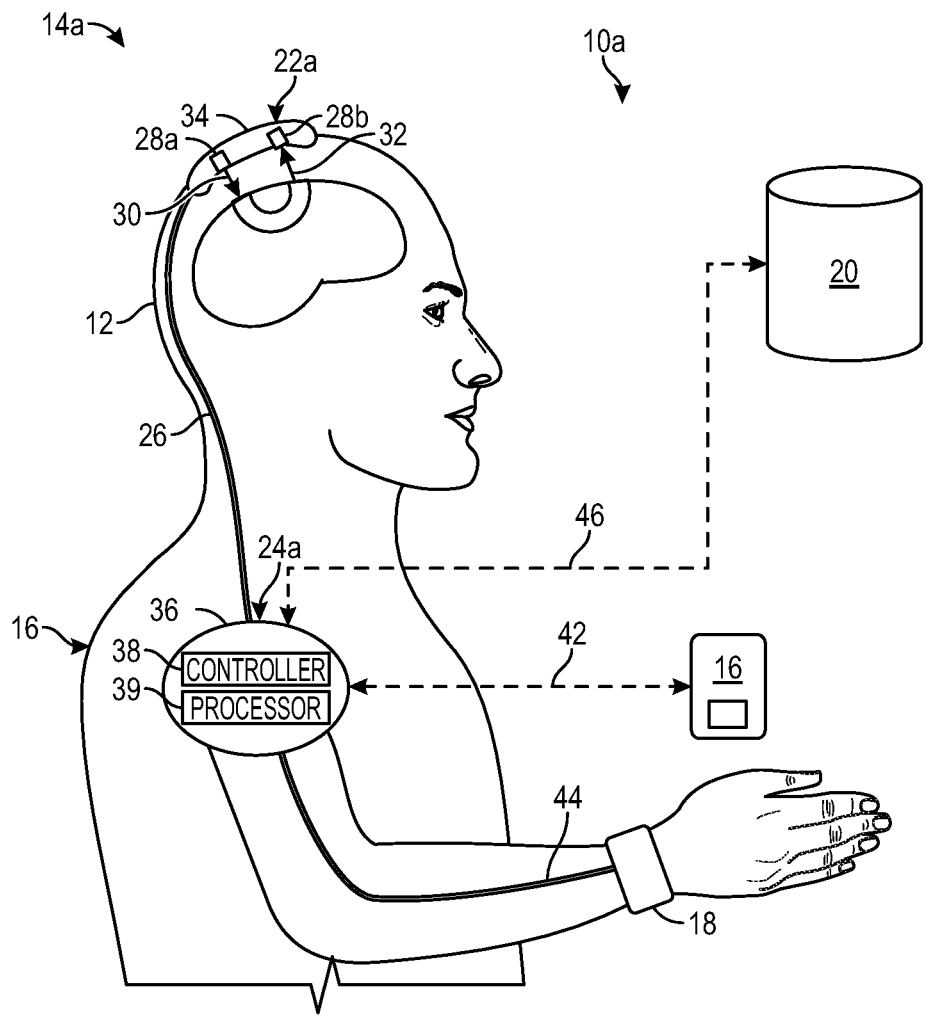
FIG. 9 is a view of one specific physical embodiment of the non-invasive mental state awareness system of FIG. 1, the non-invasive mental state modulation system of FIG. 3, or the non-invasive mental wellness tracking system of FIG. 7.

Referring to FIG. 9, a physical implementation of a system 10a (any of the mental state awareness system 10 of FIG. 1, the mental state modulation system 10' of FIG. 3, or the mental wellness tracking system 10" of FIG. 7) will now be described. The system 10a comprises an optically-based non-invasive brain interface assembly 14a, which may, e.g., incorporate any one or more of the neural activity detection technologies described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration" (now U.S. Pat. No. 10,420,469), U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. patent application Ser. No. 16/533,133, entitled "Time-Of-Flight Optical Measurement And Decoding Of Fast-Optical Signals," U.S. patent application Ser. No. 16/565,326, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Patent Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Patent Application Ser. No. 62/855,360, entitled "Interferometric Parallel Detection Using Digital Rectification and Integration", U.S. Provisional Patent Application Ser. No. 62/855,380, entitled "Interferometric Parallel Detection Using Analog Data Compression," U.S. Provisional Patent Application Ser. No. 62/855,405, entitled "Partially Balanced Interferometric Parallel Detection," which are all expressly incorporated herein by reference.

The brain interface assembly 14a includes a wearable unit 22a configured for being applied to the user 12, and in this case, worn on the head of the user 12; and an auxiliary head-worn or non-head-worn unit 24a (e.g., worn on the neck, shoulders, chest, or arm). Alternatively, the functionality of the unit 24a may be incorporated into the head-worn unit 22a. The auxiliary non-head-worn unit 24a may be coupled to the head-worn unit 22a via a wired connection 26 (e.g., electrical wires). Alternatively, the brain interface assembly 14a may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22a and the auxiliary unit 24a.

The head-worn unit 22a comprises electronic or optical components, such as, e.g., one or more optical sources, an interferometer, one or more optical detector(s) (not shown), etc., an output port 28a for emitting sample light 30 generated by the brain interface assembly 14a into the head of the user 12, an input port 28b configured for receiving neural-encoded signal light 32 from the head of the user 12, which signal light is then detected, modulated and/or processed to determine brain activity of the user 12, and a support housing structure 34 containing the electronic or optical components, and ports 28a, 28b.

The support housing structure 34 may be shaped, e.g., have a banana, headband, cap, helmet, beanie, other hat shape, or other shape adjustable and conformable to the user's head, such that the ports 28a, 28b are in close contact with the outer skin of the head, and in this case, the scalp of the user 12. The support housing structure 34 may be made out of any suitable cloth, soft polymer, plastic, hard shell, and/or any other suitable material as may serve a particular implementation. In an alternative embodiment, optical fibers (not shown) may be respectively extended from the ports 28a, 28b, thereby freeing up the requirement that the ports 28a, 28b be disposed in close proximity to the surface of the head. In any event, an index matching fluid may be used to reduce reflection of the light generated by the head-worn unit 22a from the outer skin of the scalp. An adhesive, strap, or belt (not shown) can be used to secure the support housing structure 34 to the head of the user 12.

The auxiliary unit 24a comprises a housing 36 containing a controller 38 and a processor 40. The controller 38 is configured for controlling the operational functions of the head-worn unit 22a, whereas the processor 40 is configured for processing the neural-encoded signal light 32 acquired by the head-worn unit 22a to detect and localize the brain activity of the user 12, as well as to determine the mental state of the user 12 based on the brain activity of the user 12 if not performed by other processing units in the system 10a. The auxiliary unit 24a may additionally include a power supply (which if head-worn, may take the form of a rechargeable or non-chargeable battery), a control panel with input/output functions, a display, and memory. Alternatively, power may be provided to the auxiliary unit 24a wirelessly (e.g., by induction).

The functionalities of the peripheral device 16, the biofeedback device 18, and database, server, or cloud structure 20 may be the same as described above with respect to the mental state awareness system 10 of FIG. 1, the mental state modulation system 10' of FIG. 3, or the mental wellness tracking system 10" of FIG. 7

The peripheral device 16 is coupled to the auxiliary unit 24a of the brain interface assembly 14a (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral device 16 and the brain interface assembly 14a (and/or the biofeedback device 18). In an alternative embodiment, the biofeedback device 18 is not required. Alternatively, a wired connection between the peripheral device 16 and the brain interface assembly 14a (and/or the biofeedback device 18) may be used.

The biofeedback device 18 is coupled to the brain interface assembly 14a (and in this case, to the auxiliary unit 24a) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24a of the brain interface assembly 14a and the biofeedback device 18 may be used.

The database, server, or cloud structure 20 may be coupled to the auxiliary unit 24a of the brain interface assembly 14a (and/or the peripheral device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24a of the brain interface assembly 14a (and/or the peripheral device 16 and biofeedback device 18) may be used.

Figure 10:
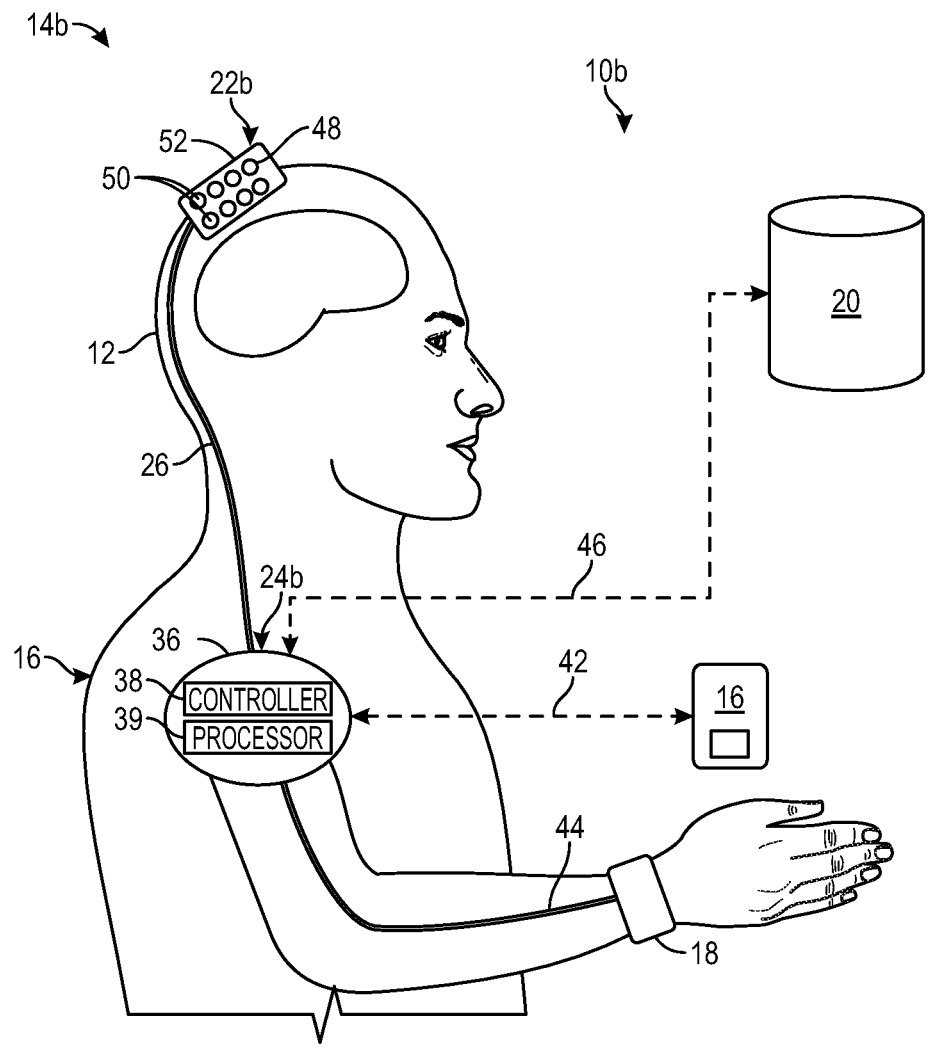
FIG. 10 is a view of another specific physical embodiment of the non-invasive mental state awareness system of FIG. 1, the non-invasive mental state modulation system of FIG. 3, or the non-invasive mental wellness tracking system of FIG. 7.

Referring to FIG. 10 a physical implementation of another system 10b (any of the mental state awareness system 10 of FIG. 1, the mental state modulation system 10' of FIG. 3, or the mental wellness tracking system 10" of FIG. 7) will now be described. The system 10b comprises an optically-based non-invasive brain interface assembly 14b, which may, e.g., incorporate any one or more of the neural activity detection technologies described in U.S. Non-Provisional patent application Ser. No. 16/051,462, entitled "Fast-Gated Photodetector Architecture Comprising Dual Voltage Sources with a Switch Configuration" (now U.S. Pat. No. 10,158, 038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340,408), U.S. patent application Ser. No. 16/283,730, entitled "Stacked Photodetector Assemblies" (now U.S. Pat. No. 10,515,993), U.S. patent application Ser. No. 16/544,850, entitled "Wearable Systems with Stacked Photodetector Assemblies," U.S. Provisional Patent Application Ser. No. 62/880,025, entitled "Photodetector Architectures for Time-Correlated Single Photon Counting," U.S. Provisional Patent Application Ser. No. 62/889,999, entitled "Photodetector Architectures for Efficient Fast-Gating," U.S. Provisional Patent Application Ser. No. 62/906, 620, entitled "Photodetector Systems with Low-Power Time-To-Digital Converter Architectures," U.S. Provisional Patent Application Ser. No. 62/979,866 entitled "Optical Module Assemblies," U.S. Provisional Patent Application Ser. No. 62/992,486 entitled "Laser Diode Driver Circuit with Adjustable Turn-Off and Turn-On Current Slew Rates," U.S. Provisional Patent Application Ser. No. 62/992,491 entitled "Multiplexing Techniques for Interference Reduction in Time-Correlated Signal Photon Counting," U.S. Provisional Patent Application Ser. No. 62/992,493 entitled "SPAD Bias Compensation," U.S. Provisional Patent Application Ser. No. 62/992,497 entitled "Measurement Window Calibration for Detection of Temporal Point Spread Function," U.S. Provisional Patent Application Ser. No. 62/992, 499 entitled "Techniques for Determining Impulse Response of SPAD and TDC Systems," U.S. Provisional Patent Application Ser. No. 62/992,502 entitled "Histogram Based Code Density Characterization and Correction in Time-Correlated Single Photon Counting," U.S. Provisional Patent Application Ser. No. 62/992,506 entitled "Selectable Resolution Modes in an Optical Measurement System," U.S. Provisional Patent Application Ser. No. 62/992,510 entitled "Hierarchical Bias Generation for Groups of SPAD Detectors," U.S. Provisional Patent Application Ser. No. 62/992, 512 entitled "Detection and Removal of Motion Artifacts in a Wearable Optical Measurement System," U.S. Provisional Patent Application Ser. No. 62/992,526 entitled "Dynamic Range Improvement from Highly Parallel Arrays and SPADs," U.S. Provisional Patent Application Ser. No. 62/992,529 entitled "Single-Photon Avalanche Diode (SPAD) Bias Constant Charge," U.S. Provisional Patent Application Ser. No. 62/992,536 entitled "Calibration of SPAD ToF Systems Based on Per Pixel Dark Count Rate," U.S. Provisional Patent Application Ser. No. 62/992,543 entitled "Estimation of Source-Detector Separation in an Optical Measurement System," U.S. Provisional Patent Application Ser. No. 62/992,550 entitled "Wearable Module for an Optical Measurement or Hybrid Technology Neural Recording System Where the Module Assemblies are Configured for Tiling Multiple Modules Together for Targeted and/or Complete Head Coverage," U.S. Provisional Patent Application Ser. No. 62/992,552 entitled "Wearable Devices for a Brain Computer Interface (BCI) System Where the Wearable Device Includes Conforming Headset Fixation," U.S. Provisional Patent Application Ser. No. 62/992,555 entitled "Integrated Detector Assemblies for a Wearable Module of an Optical Measurement System," U.S. Provisional Patent Application Ser. No. 62/992,559 entitled "Integrated Detector Assemblies for a Wearable Module of an Optical Measurement Where the Detector Assemblies Include Spring Loaded Light Pipes," and U.S. Provisional Patent Application Ser. No. 62/992,567 entitled "Integrated Light Source Assembly with Laser Coupling for a Wearable Optical Measurement System," which are all expressly incorporated herein by reference.

The brain interface assembly 14b includes a head-worn unit 22b that is configured for being applied to the user 12, and in this case, worn on the head of the user 12; and an auxiliary non-head-worn unit 24b (e.g., worn on the neck, shoulders, chest, or arm). Alternatively, the functionality of the unit 24b may be incorporated into the head-worn unit 22b, as described below. The auxiliary non-head-worn unit 24b may be coupled to the head-worn unit 22b via a wired connection 26 (e.g., electrical wires). Alternatively, the brain interface assembly 14b may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22b and the auxiliary unit 24b.

The head-worn unit 22b includes one or more light sources 48 configured for generating light pulses. The light source(s) 48 may be configured for generating one or more light pulses at one or more wavelengths that may be applied to a desired target (e.g., a target within the brain). The light source(s) 48 may be implemented by any suitable combination of components. For example, light source(s) 48 described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

The head-worn unit 22b includes a plurality of photodetector units 50, e.g., comprising single-photon avalanche diodes (SPADs) configured for detecting a single photon (i.e., a single particle of optical energy) in each of the light pulses. For example, an array of these sensitive photodetector units can record photons that reflect off of tissue within the brain in response to application of one or more of the light pulses generated by the light sources 48. Based on the time it takes for the photons to be detected by the photodetector units, neural activity and other attributes of the brain can be determined or inferred.

Photodetector units that employ the properties of a SPAD are capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD, referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon. In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

It will be recognized that in some alternative embodiments, the head-worn unit 22b may include a single light source 48 and/or single photodetector unit 50. For example, brain interface system 14b may be used for controlling a single optical path and for transforming photodetector pixel measurements into an intensity value that represents an optical property of a brain tissue region. In some alternative embodiments, the head-worn unit 22b does not include individual light sources. Instead, a light source configured to generate the light that is detected by the photodetector may be included elsewhere in the brain interface system 14b. For example, a light source may be included in the auxiliary unit 24b.

The head-worn unit 22b further comprises a support housing structure 52 containing the light source(s) 48, photodetector units 50, and other electronic or optical components. As will be described in further detail below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12. The support housing structure 52 may be made out of any suitable cloth, soft polymer, plastic, hard shell, and/or any other suitable material as may serve a particular implementation.

The auxiliary unit 24b comprises the housing 36 containing the controller 38 and the processor 40. The controller 38 is configured for controlling the operational functions of the head-worn unit 22b, whereas the processor 40 is configured for processing the photons acquired by the head-worn unit 22b to detect and localize the brain activity of the user 12, as well as to determine the mental state of the user 12 based on the brain activity of the user 12 if not performed by other processing units in the system 10b. The auxiliary unit 24b may additionally include a power supply (which if head-worn, may take the form of a rechargeable or non-chargeable battery), a control panel with input/output functions, a display, and memory. Alternatively, power may be provided to the auxiliary unit 24b wirelessly (e.g., by induction).

The functionalities of the peripheral device 16, the biofeedback device 18, and database, server, or cloud structure 20 may be the same as described above with respect to the mental state awareness system 10 of FIG. 1, the mental state modulation system 10' of FIG. 3, or the mental wellness tracking system 10" of FIG. 7.

The peripheral device 16 is coupled to the auxiliary unit 24b of the brain interface assembly 14b (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral device 16 and the brain interface assembly 14b (and/or the biofeedback device 18). Alternatively, a wired connection between the peripheral device 16 and the brain interface assembly 14c (and/or the biofeedback device 18) may be used.

The biofeedback device 18 is coupled to the brain interface assembly 14b (and in this case, to the auxiliary unit 24b) via a wired connection 44 (e.g., electrical wires). In an alternative embodiment, the biofeedback device 18 is not required. Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24b of the brain interface assembly 14c and the biofeedback device 18 may be used.

The database, server, or cloud structure 20 may be coupled to the auxiliary unit 24b of the brain interface assembly 14b (and/or the peripheral device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24b of the brain interface assembly 14b (and/or the peripheral device 16 and biofeedback device 18) may be used.

Referring now to FIGS. 11A-11D, different embodiments of the brain interface assembly 14b will be described. Such brain interface assemblies 14b may communicate wirelessly or via wire with the peripheral device 16, the biofeedback device 18, and database, server, cloud structure 20, as described above. In an alternative embodiment, the biofeedback device 18 is not required. Each of the brain interface assemblies 14b described below comprises a head-worn unit 22b having a plurality of photodetector units 50 and a support housing structure 52 in which the photodetector units 50 are embedded. Each of the photodetector units 50 may comprise, e.g., a SPAD, voltage sources, capacitors, switches, and any other circuit components (not shown) required to detect photons. Each of the brain interface assemblies 14b may also comprise one or more light sources (not shown) for generating light pulses, although the source of such light may be derived from ambient light in some cases. Each of brain interface assemblies 14b may also comprise a control/processing unit 54, such as, e.g., a control circuit, time-to-digital (TDC) converter, and signal processing circuit for controlling the operational functions of the photodetector units 50 and any light source(s), and processing the photons acquired by photodetector units 50 to detect and localize the brain activity of the user 12. As will be described in further detail below, the control/processing unit 54 may be contained in the head-worn unit 22b or may be incorporated into a self-contained auxiliary unit. As will be set forth below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12.

Figure 11A:
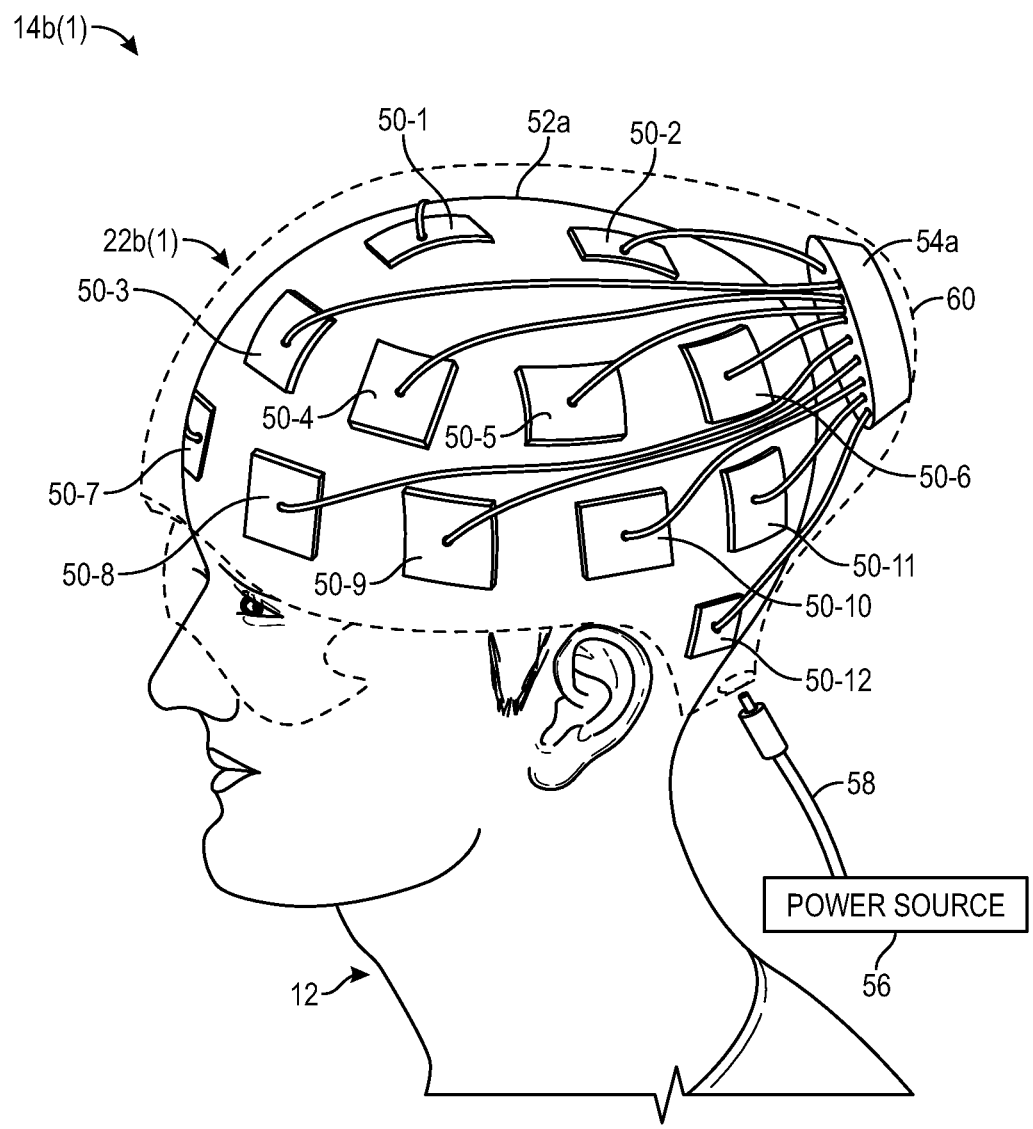
FIG. 11A-11D illustrate exemplary non-invasive wearable devices as used with the system of FIG. 10.

As shown in FIG. 11A, a brain interface assembly 14b(1) comprises a head-worn unit 22b(1) and a power source 56 coupled to the head-worn unit 22b(1) via a power cord 58. The head-worn unit 22b(1) includes the photodetector units 50 (shown as 50-1 through 50-12) and a control/processing unit 54a. The head-worn unit 22b(1) further includes a support housing structure 52a that takes a form of a cap that contains the photodetector units 50 and control/processing unit 54a. The material for the cap 52a may be selected out of any suitable cloth, soft polymer, plastic, hard shell, and/or any other suitable material as may serve a particular implementation. The power source 56 may be implemented by a battery and/or any other type of power source configured to provide operating power to the photodetector units 50, control/processing unit 54a, and any other component included within the brain interface assembly 22b(1) via the power cord 58. The head-worn unit 22b(1) optionally includes a crest or other protrusion 60 formed in the cap 52a for providing means of carrying a control/processing unit 54a.

Figure 11B:
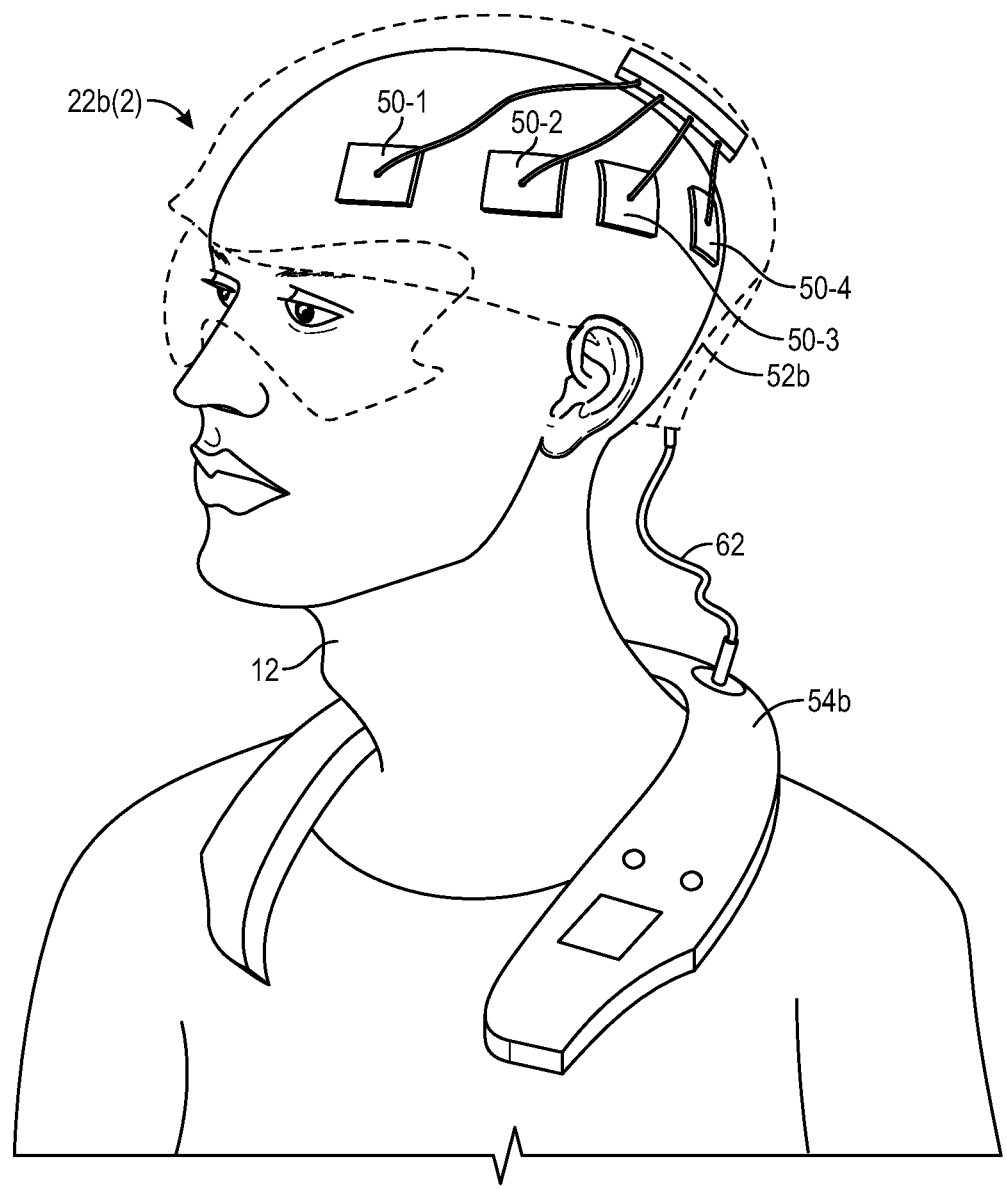

As shown in FIG. 11B, a brain interface assembly 14b(2) comprises a head-worn unit 22b(2) and a control/processing unit 54b coupled to the head-worn unit 22b(2) via a wired connection 62. The head-worn unit 22b(2) includes the photodetector units 50 (shown as 50-1 through 50-4), and a support housing structure 52b that takes a form of a helmet containing the photodetector units 50. The material for the helmet 52b may be selected out of any suitable polymer, plastic, hard shell, and/or any other suitable material as may serve a particular implementation. Unlike the control/processing unit 54a of the brain interface assembly 14b(1) illustrated in FIG. 11A, which is contained in the head-worn unit 22b(1), the control/processing unit 54b is self-contained, and may take the form of a garment (e.g., a vest, partial vest, or harness) for being worn on the shoulders of the user 12. The self-contained control/processing unit 54b may additionally include a power supply (which if head-worn, may take the form of a rechargeable or non-chargeable battery), a control panel with input/output functions, a display, and memory. Alternatively, power may be provided to the self-contained control/processing unit 54b wirelessly (e.g., by induction).

Figure 11C:
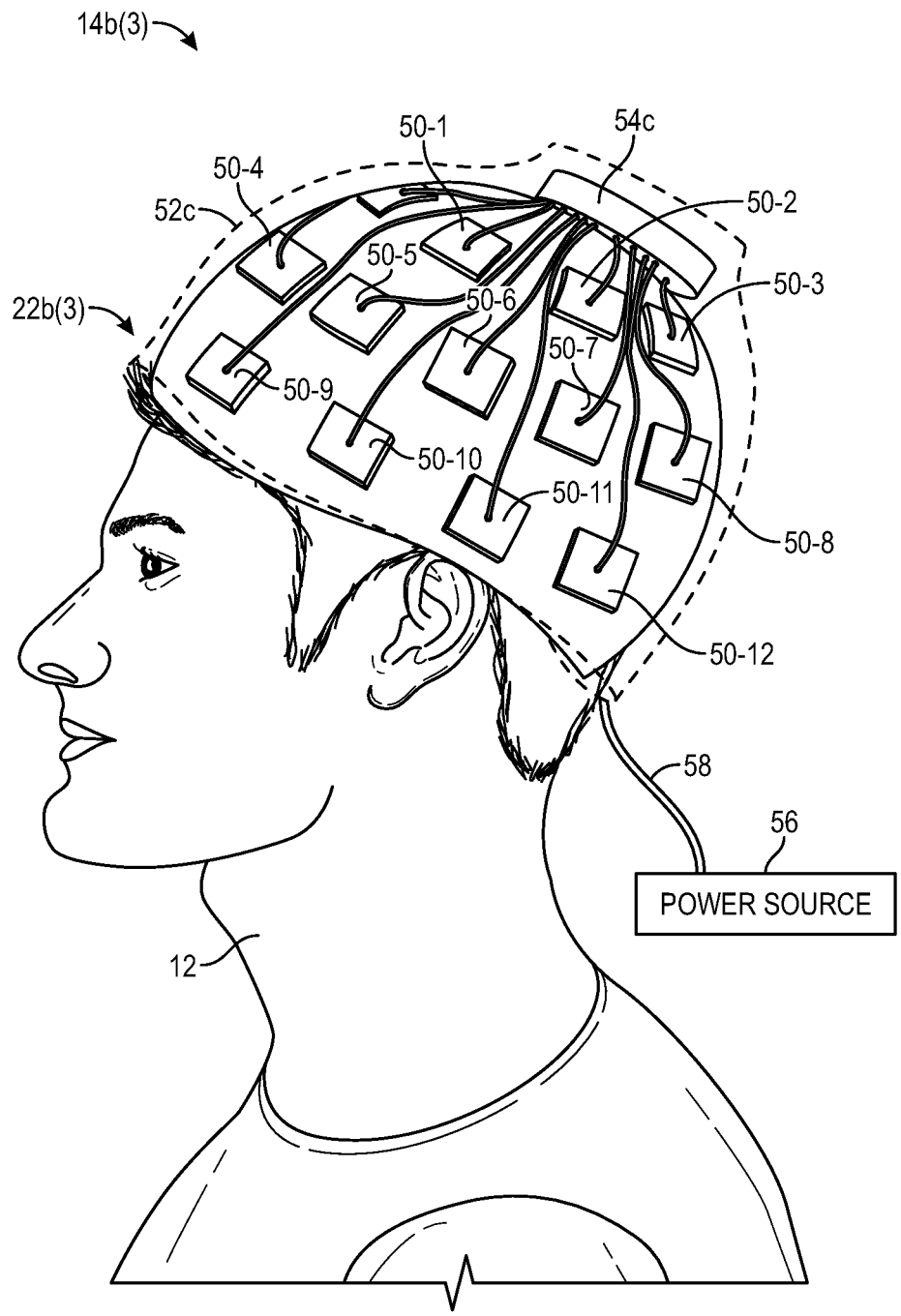

As shown in FIG. 11C, a brain interface assembly 14b(3) comprises a head-worn unit 22b(3) and a power source 56 coupled to the head-worn unit 22b(3) via a power cord 58. The head-worn unit 22b(3) includes the photodetector units 50 (shown as 50-1 through 50-12) and a control/processing unit 54c. The head-worn unit 22b(3) further includes a support housing structure 52c that takes a form of a beanie that contains the photodetector units 50 and control/processing unit 54c. The material for the beanie 52c may be selected out of any suitable cloth, soft polymer, plastic, and/or any other suitable material as may serve a particular implementation. The power source 56 may be implemented by a battery and/or any other type of power source configured to provide operating power to the photodetector units 50, control/processing unit 54c, and any other component included within the brain interface assembly 22b(3) via a wired connection 58.

Figure 11D:
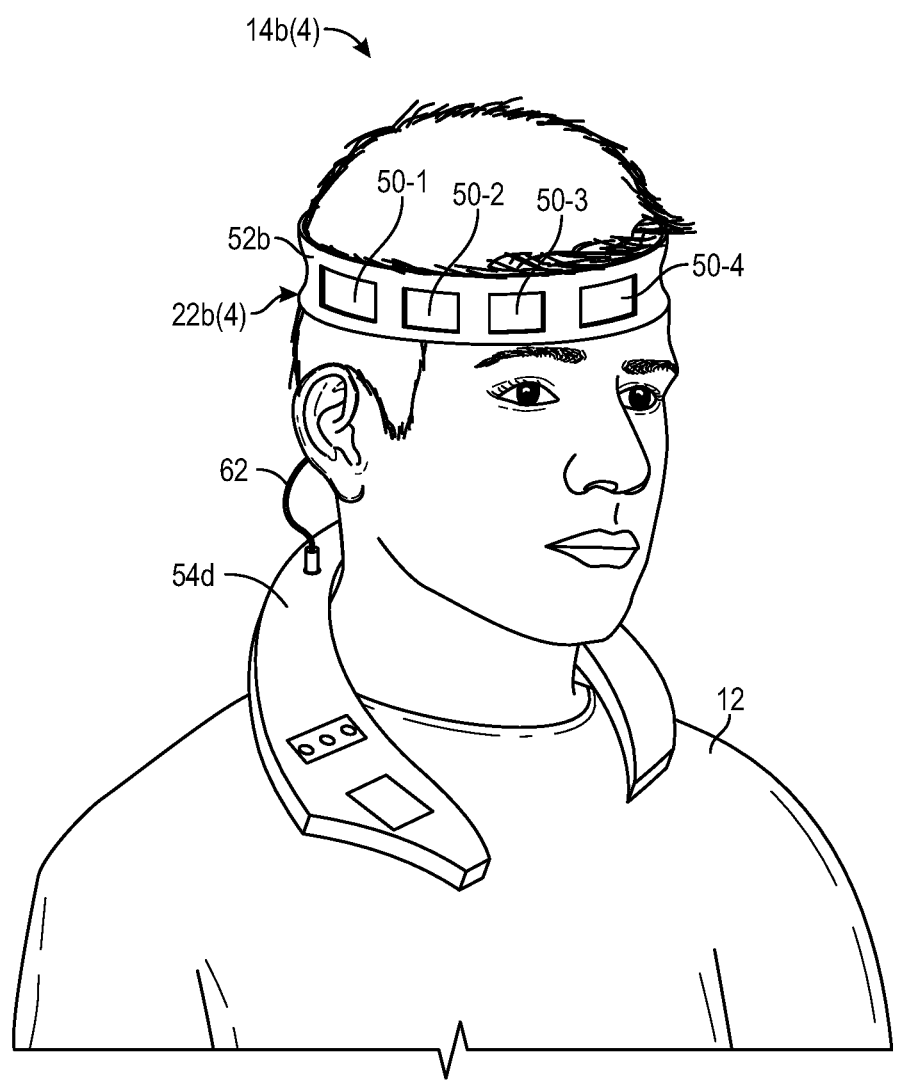

As shown in FIG. 11D, a brain interface assembly 14b(4) comprises a head-worn unit 22b(4) and a control/processing unit 54d coupled to the head-worn unit 22b(4) via a wired connection 62. The head-worn unit 22b(4) includes the photodetector units 50 (shown as 50-1 through 50-4), and a support housing structure 52d that takes a form of a headband containing the photodetector units 50. The material for the headband 52d may be selected out of any suitable cloth, soft polymer, plastic, hard shell, and/or any other suitable material as may serve a particular implementation. The control/processing unit 54d is self-contained, and may take the form of a garment (e.g., a vest, partial vest, or harness) for being worn on the shoulders of the user 12. The self-contained control/processing unit 54d may additionally include a power supply (which if head-worn, may take the form of a rechargeable or non-chargeable battery), a control panel with input/output functions, a display, and memory. Alternatively, power may be provided to the self-contained control/processing unit 54d wirelessly (e.g., by induction).

Figure 12:
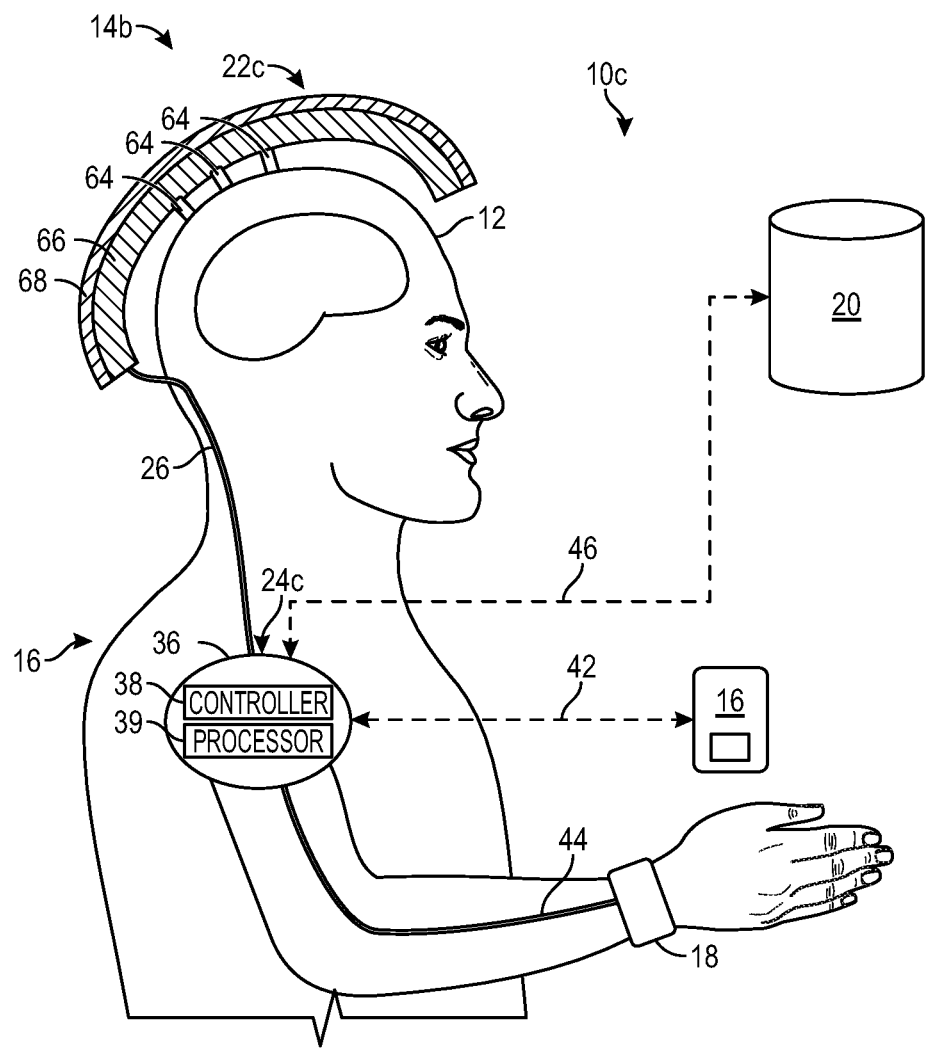
FIG. 12 is a view of still another physical specific embodiment of the non-invasive mental state awareness system of FIG. 1, the non-invasive mental state modulation system of FIG. 3, or the non-invasive mental wellness tracking system of FIG. 7.

Referring to FIG. 12, a physical implementation of still another system 10c (any of the mental state awareness system 10 of FIG. 1, the mental state modulation system 10' of FIG. 3, or the mental wellness tracking system 10" of FIG. 7) will now be described. The system 10c comprises a magnetically-based non-invasive brain interface assembly 14c, which may, e.g., incorporate any one or more of the neural activity detection technologies described in U.S. patent application Ser. No. 16,428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems entitled "Systems and Methods Including Multi-Mode Operation of Optically Pumped Magnetometer(S)," U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Patent Application Ser. No. 62/858,636, entitled "Integrated Magnetometer Arrays for Magnetoencephalography (MEG) Detection Systems and Methods," U.S. Provisional Patent Application Ser. No. 62/836,421, entitled "Systems and Methods for Suppression of Non-Neural Interferences in Magnetoencephalography (MEG) Measurements," U.S. Provisional Patent Application Ser. No. 62/842,818 entitled "Active Shield Arrays for Magnetoencephalography (MEG)," U.S. Provisional Patent Application Ser. No. 62/926,032 entitled "Systems and Methods for Multiplexed or Interleaved Operation of Magnetometers," U.S. Provisional Patent Application Ser. No. 62/896,929 entitled "Systems and Methods having an Optical Magnetometer Array with Beam Splitters," U.S. Provisional Patent Application Ser. No. 62/960,548 entitled "Methods and Systems for Fast Field Zeroing for Magnetoencephalography (MEG)," U.S. Provisional Patent Application Ser. No. 62/967,787 entitled "Single Controller for Wearable Sensor Unit that Includes an Array Of Magnetometers," U.S. Provisional Patent Application Ser. No. 62/967,797 entitled "Systems and Methods for Measuring Current Output By a Photodetector of a Wearable Sensor Unit that Includes One or More Magnetometers," U.S. Provisional Patent Application Ser. No. 62/967,803 entitled "Interface Configurations for a Wearable Sensor Unit that Includes One or More Magnetometers," U.S. Provisional Patent Application Ser. No. 62/967,804 entitled "Systems and Methods for Concentrating Alkali Metal Within a Vapor Cell of a Magnetometer Away from a Transit Path of Light," U.S. Provisional Patent Application Ser. No. 62/967,813 entitled "Magnetic Field Generator for a Magnetic Field Measurement System," U.S. Provisional Patent Application Ser. No. 62/967,818 entitled "Magnetic Field Generator for a Magnetic Field Measurement System," U.S. Provisional Patent Application Ser. No. 62/967,823 entitled "Magnetic Field Measurement Systems Including a Plurality of Wearable Sensor Units Having a Magnetic Field Generator," U.S. Provisional Patent Application Ser. No. 62/975,709 entitled "Self-Calibration of Flux Gate Offset and Gain Drift To Improve Measurement Accuracy of Magnetic Fields from the Brain Using a Wearable System," U.S. Provisional Patent Application Ser. No. 62/975,693 entitled "Nested and Parallel Feedback Control Loops for Ultra-Fine Measurements of Magnetic Fields from the Brain Using a Wearable MEG System," U.S. Provisional Patent Application Ser. No. 62/975,719 entitled "Estimating the Magnetic Field at Distances from Direct Measurements to Enable Fine Sensors to Measure the Magnetic Field from the Brain Using a Wearable System," U.S. Provisional Patent Application Ser. No. 62/975,723 entitled "Algorithms that Exploit Maxwell's Equations and Geometry to Reduce Noise for Ultra-Fine Measurements of Magnetic Fields from the Brain Using a Wearable MEG System," U.S. Provisional Patent Application Ser. No. 62/975,727 entitled "Optimal Methods to Feedback Control and Estimate Magnetic Fields to Enable a Wearable System to Measure Magnetic Fields from the Brain," and U.S. Provisional Patent Application Ser. No. 62/983,406 entitled "Two Level Magnetic Shielding of Magnetometers," which are all expressly incorporated herein by reference.

The brain interface assembly 14c (shown in FIG. 12) includes a magnetoencephalography (MEG) head-worn unit 22c that is configured for being applied to the user 12, and in this case, worn on the head of the user 12; and an auxiliary non-head-worn unit 24c (e.g., worn on the neck, shoulders, chest, or arm). Alternatively, the functionality of the unit 24c may be incorporated into the head-worn unit 22c, as described below. The auxiliary non-head-worn unit 24c may be coupled to the head-worn unit 22c via a wired connection 26 (e.g., electrical wires). Alternatively, the brain interface assembly 14c may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22c and the auxiliary unit 24c.

The head-worn unit 22c includes a plurality of optically pumped magnetometers (OPMs) 64 or other suitable magnetometers to measure biologically generated magnetic fields from the brain of the user 12 and a passive shield 66 (and/or flux concentrators). By placing the passive shield 66 over the head of the user 12, the ambient background magnetic field arising from areas outside the passive shield 66 is greatly decreased and the magnetometers 64 can measure or detect magnetic fields from activity occurring in the brain of the user 12 due to the reduction in the ambient background magnetic field.

An OPM is used in an optical magnetometry system used to detect a magnetic field that propagates through the human head. Optical magnetometry can include the use of optical methods to measure a magnetic field with very high accuracy—on the order of $1 \times 10^{-15}$ Tesla. Of particular interest for their high-sensitivity, an OPM can be used in optical magnetometry to measure weak magnetic fields. (The Earth's magnetic field is typically around 50 micro Tesla). In at least some systems, the OPM has an alkali vapor gas cell that contains alkali metal atoms in a combination of gas, liquid, or solid states (depending on temperature). The gas cell may contain a quenching gas, buffer gas, or specialized anti-relaxation coatings or any combination thereof. The size of the gas cells can vary from a fraction of a millimeter up to several centimeters, allowing the practicality of OPMs to be used with wearable non-invasive brain interface devices.

The head-worn unit 22c further comprises a support housing structure 68 containing the OPMs 64, passive shield 66, and other electronic or magnetic components. As will be described in further detail below, the support housing structure 68 may be shaped, e.g., have a banana, headband, cap, helmet, beanie, other hat shape, or other shape adjustable and conformable to the user's head, such that the OPMs 64 are in close contact with the outer skin of the head, and in this case, the scalp of the user 12. The support housing structure 68 may be made out of any suitable cloth, soft polymer, plastic, hard shell, and/or any other suitable material as may serve a particular implementation.

The auxiliary unit 24c comprises the housing 36 containing the controller 38 and the processor 40. The controller 38 is configured for controlling the operational functions of the head-worn unit 22c, whereas the processor 40 is configured for processing the magnetic fields detected by the head-worn unit 22c to detect and localize the brain activity of the user 12, as well as to determine the mental state of the user 12 based on the brain activity of the user 12 if not performed by other processing units in the system 10c. The auxiliary unit 24c may additionally include a power supply (which if head-worn, may take the form of a rechargeable or non-chargeable battery), a control panel with input/output functions, a display, and memory. Alternatively, power may be provided to the auxiliary unit 24c wirelessly (e.g., by induction).

The functionalities of the peripheral device 16, the biofeedback device 18, and database, server, or cloud structure 20 may be the same as described above with respect to the mental state awareness system 10 of FIG. 1, the mental state modulation system 10' of FIG. 3, or the mental wellness tracking system 10" of FIG. 7.

The peripheral device 16 is coupled to the auxiliary unit 24c of the brain interface assembly 14c (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral device 16 and the brain interface assembly 14c (and/or the biofeedback device 18). In an alternative embodiment, the biofeedback device 18 is not required. Alternatively, a wired connection between the peripheral device 16 and the brain interface assembly 14c (and/or the biofeedback device 18) may be used.

The biofeedback device 18 is coupled to the brain interface assembly 14c (and in this case, to the auxiliary unit 24c) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24c of the brain interface assembly 14c and the biofeedback device 18 may be used.

The database, server, or cloud structure 20 may be coupled to the auxiliary unit 24c of the brain interface assembly 14c (and/or the peripheral device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24c of the brain interface assembly 14c (and/or the peripheral device 16 and biofeedback device 18) may be used.

Figure 13A:
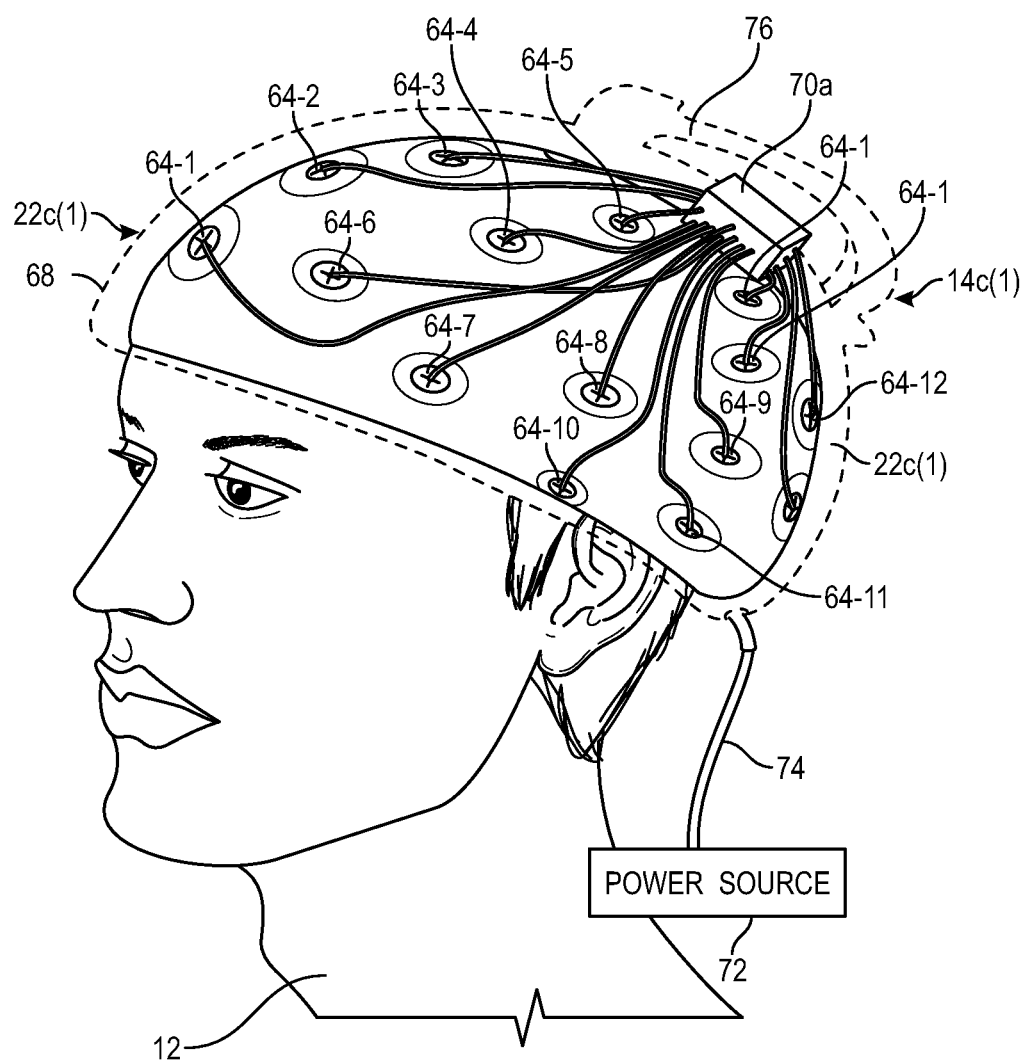
FIG. 13A-13C illustrate exemplary non-invasive wearable devices as used with the system of FIG. 12.
Figure 13B:
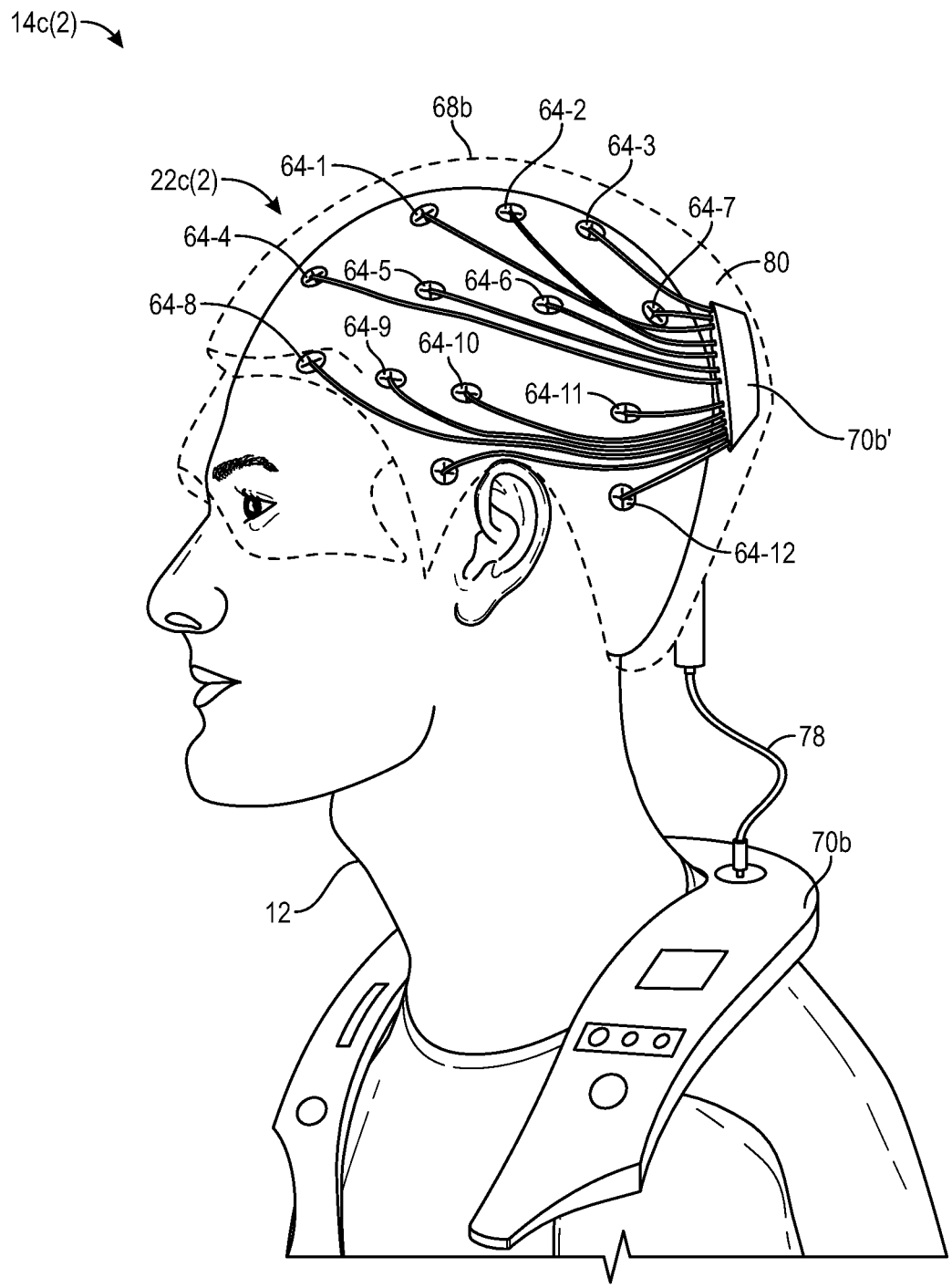
Figure 13C:
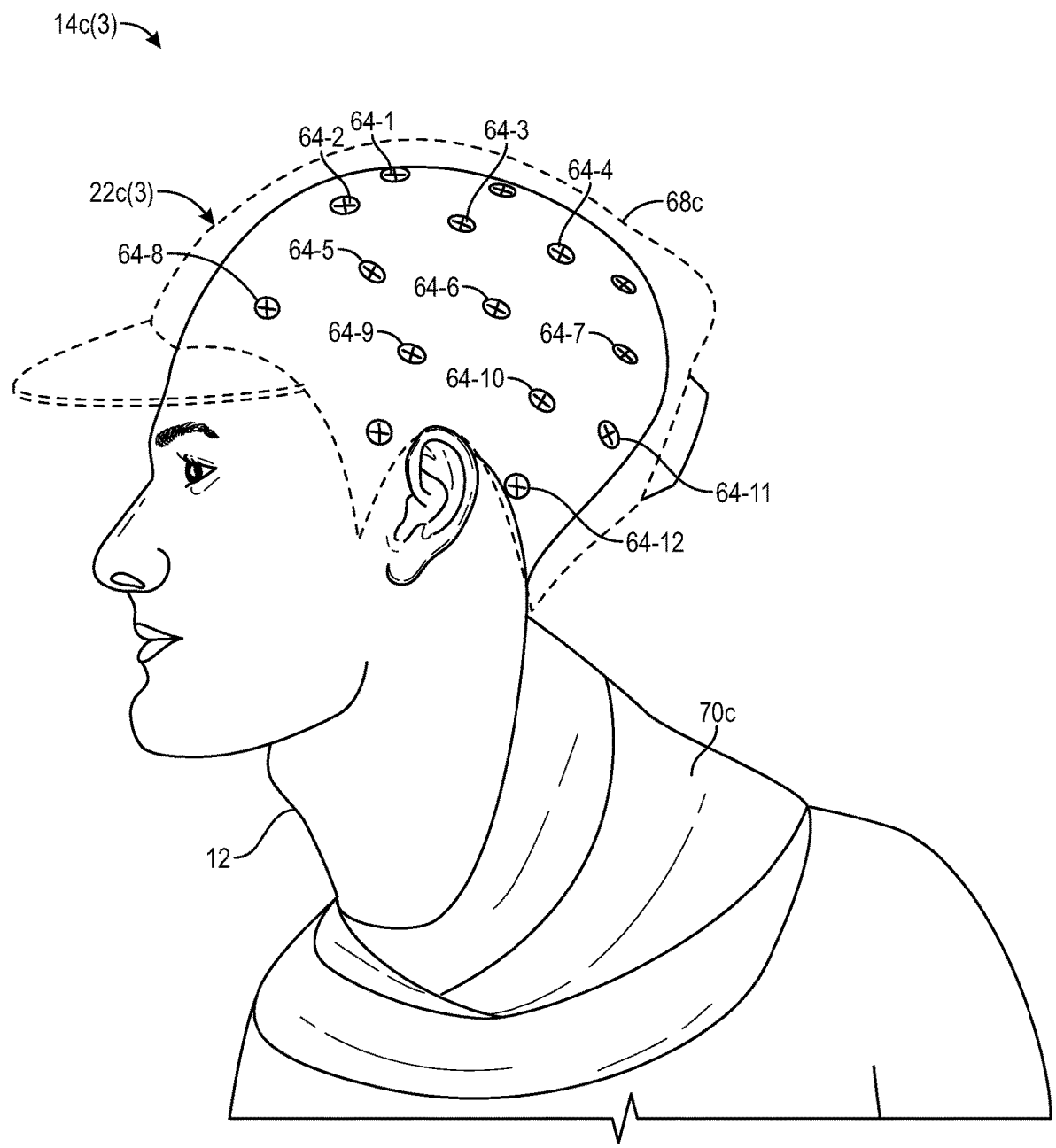

Referring now to FIGS. 13A-13C, different embodiments of the brain interface assembly 14c will be described. Such brain interface assemblies 14c may communicate wirelessly or via wire with the peripheral device 16, biofeedback device 18, and database, server, cloud structure 20, as described above. Each of the brain interface assemblies 14c described below comprises a head-worn unit 22c having a plurality of OPMs 64, a passive shield 66, and a support housing structure 68 in which the OPMs 64 and passive shield 66 are embedded. Each of brain interface assemblies 14c may also comprise a control/processing unit 70 for controlling the operational functions of the OPMs 64, and processing the magnetic fields detected by the OPMs 64 to detect and localize the brain activity of the user 12. As will be described in further detail below, the control/processing unit 70 may be contained in the head-worn unit 22c or may be incorporated into a self-contained auxiliary unit. As will be set forth below, the support housing structure 68 may be shaped, e.g., have a banana, headband, cap, helmet, beanie, other hat shape, or other shape adjustable and conformable to the user's head, such that the magnetometers 64 are in close contact with the outer skin of the head, and in this case, the scalp of the user 12.

As shown in FIG. 13A, a brain interface assembly 14c(1) comprises a head-worn unit 22c(1) and a power source 72 coupled to the head-worn unit 22c(1) via a wired connection 74. The head-worn unit 22c(1) includes the OPMs 64 (shown as 64-1 through 64-12) and a control/processing unit 70a. The head-worn unit 22c(1) further includes a support housing structure 68a that takes a form of a helmet that contains the OPMs 64, passive shield 66, and control/processing unit 70a. The material for the helmet 68a may be selected out of any suitable cloth, soft polymer, plastic, hard shell, and/or any other suitable material as may serve a particular implementation. The power source 72 may be implemented by a battery and/or any other type of power source configured to provide operating power to the magnetometers 64, control/processing unit 70a, and any other component included within the brain interface assembly 22c(1) via the wired connection 74. The head-worn unit 22c(1) optionally includes a handle 76 affixed to the helmet 68a for providing a convenient means of carrying the head-worn unit 22c(1).

As shown in FIG. 13B, a brain interface assembly 14c(2) comprises a head-worn unit 22c(2) and a control/processing unit 70b coupled to the head-worn unit 22c(2) via a wired connection 78. The head-worn unit 22c(2) includes the OPMs 64 (shown as 64-1 through 64-12), and a support housing structure 68c that takes a form of a helmet that contains the OPMs 64 and passive shield 66. The material for the helmet 68c may be selected out of any suitable cloth, soft polymer, plastic, hard shell, and/or any other suitable material as may serve a particular implementation. Unlike the control/processing unit 70a of the brain interface assembly 14c(1) illustrated in FIG. 11A, which is contained in the head-worn unit 22c(1), the control/processing unit 70b is self-contained, and may take the form of a garment (e.g., a vest, partial vest, or harness) for being worn on the shoulders of the user 12. The self-contained control/processing unit 70b may additionally include a power supply (which if head-worn, may take the form of a rechargeable or non-chargeable battery), a control panel with input/output functions, a display, and memory. Alternatively, power may be provided to the self-contained control/processing unit 70b wirelessly (e.g., by induction). The head-worn unit 22c(1)

optionally includes a crest or other protrusion 80 formed in the helmet 68*c* for providing means of carrying a control/processing unit 70*b′*.

As shown in FIG. 13C, a brain interface assembly 14*c*(3) comprises a head-worn unit 22*c*(3) and a control/processing unit 70*c*. The head-worn unit 22*c*(3) includes the OPMs 64 (shown as 64-1 through 64-12), and a support housing structure 68*c* that takes a form of a baseball cap that contains the OPMs 64 and passive shield 66. The material for baseball cap 68*c* may be selected out of any suitable cloth, soft polymer, plastic, hard shell, and/or any other suitable material as may serve a particular implementation. The control/processing unit 70*c* is self-contained, and may take the form of a garment (e.g., scarf) for being worn around the neck of the user 12. The self-contained control/processing unit 70*c* may additionally include a power supply (which if head-worn, may take the form of a rechargeable or non-chargeable battery), a control panel with input/output functions, a display, and memory. Alternatively, power may be provided to the self-contained control/processing unit 70*c* wirelessly (e.g., by induction).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An entertainment system, comprising:
    a peripheral device configured for presenting an entertainment selection in a list of entertainment selections to a user in a normal life and work environment outside of a clinical setting, wherein presenting the entertainment selection to the user comprises one of presenting content of the entertainment selection of the user and presenting a title of the entertainment selection to the user;
    a non-invasive brain interface assembly configured for detecting brain activity of the user; and
    at least one processor containing software configured for determining a mental state of the user based on the detected brain activity, and in response to the determined mental state of the user, for automatically performing an action on the entertainment selection list.

2. The entertainment system of claim 1, wherein presenting the entertainment selection to the user comprises presenting content of the entertainment selection to the user.

3. The entertainment system of claim 1, wherein presenting the entertainment selection to the user comprises presenting a title of the entertainment selection to the user.

4. The entertainment system of claim 1, wherein the list of entertainment selections comprises a play list of songs.

5. The entertainment system of claim 1, wherein the determined mental state of the user is one of a first mental state and a second mental state different from the first mental state.

6. The entertainment system of claim 5,
    wherein, if the determined mental state is the first mental state, then the action automatically performed by the at least one processor is retaining the entertainment selection in the entertainment selection list; and
    wherein, if the determined mental state is the second mental state, then the action automatically performed by the at least one processor is discarding the entertainment selection from the entertainment selection list.

7. The entertainment system of claim 6,
    wherein, if the determined mental state is the first mental state, then the action automatically performed by the at least one processor is including more entertainment selections in the entertainment selection list having the same attributes as the entertainment selection presented to the user; and
    wherein, if the determined mental state is the second mental state, then the action automatically performed by the at least one processor is including less entertainment selections in the entertainment selection list having the same attributes as the entertainment selection presented to the user.

8. The entertainment system of claim 1, wherein the determined mental state of the user comprises an initial response of the user to the entertainment selection presented to the user.

9. The entertainment system of claim 1, wherein the peripheral device contains software configured for sequentially presenting content of the entertainment selection list to the user.

10. The entertainment system of claim 9, wherein the software contained in the peripheral device is configured for sequentially presenting the content of the entertainment selection list to the user by streaming the content of the entertainment selection list to the user.

11. The entertainment system of claim 1, wherein the non-invasive brain interface assembly is one of an optical measurement assembly and a magnetic measurement assembly.

12. The entertainment system of claim 1, wherein the non-invasive brain interface assembly comprises a head-worn unit carrying at least one detector configured for detecting energy from a brain of the user.

13. The entertainment system of claim 12, wherein the non-invasive brain interface assembly comprises an auxiliary non-head-worn unit carrying processing circuitry configured for identifying the brain activity in response to detecting the energy from the brain of the user.

14. The entertainment system of claim 1, wherein at least a portion of the software of the at least one processor is contained in the peripheral device.

15. The entertainment system of claim 1, wherein the non-invasive brain interface assembly is portable and wearable.

16. A method of entertaining a user while the user is in a normal life and work environment outside of a clinical setting, comprising:
    presenting an entertainment selection from a list of entertainment selections to the user, wherein presenting the entertainment selection to the user comprises one of presenting content of the entertainment selection of the user and presenting a title of the entertainment selection to the user;
    detecting brain activity of the user while an entertainment selection in the entertainment selection list is presented to the user;
    determining a mental state of the user based on the detected brain activity; and
    automatically performing an action on the entertainment selection list in response to the determined mental state of the user.

17. The method of claim 16, wherein presenting the entertainment selection to the user comprises presenting content of the entertainment selection to the user.

18. The method of claim 16, wherein presenting the entertainment selection to the user comprises presenting a title of the entertainment selection to the user.

19. The method of claim 16, wherein the list of entertainment selections comprises a play list of songs.

20. The method of claim 16, wherein the determined mental state of the user is one of a first mental state and a second mental state different from the first mental state.

21. The method of claim 20,
wherein, if the determined mental state is the first mental state, then the performed action is retaining the entertainment selection in the entertainment selection list; and
wherein, if the determined mental state is the second mental state, then the performed action is discarding the entertainment selection from the entertainment selection list.

22. The method of claim 21,
wherein, if the determined mental state is the first mental state, then the performed action is including more entertainment selections in the entertainment selection list having the same attributes as the entertainment selection presented to the user; and
wherein, if the determined mental state is the second mental state, then the performed action is including less entertainment selections in the entertainment selection list having the same attributes as the entertainment selection presented to the user.

23. The method of claim 16, wherein the determined mental state of the user comprises an initial response of the user to the entertainment selection presented to the user.

24. The method of claim 16, further comprising sequentially presenting content of the entertainment selection list to the user.

25. The method of claim 24, wherein sequentially presenting the content of the entertainment selection list to the user comprises streaming the entertainment selection list to the user.

26. The method of claim 16, wherein detecting the brain activity of the user comprises one of optically detecting the brain activity of the user and magnetically detecting the brain activity of the user.

* * * * *